United States Patent
Mazumder et al.

(10) Patent No.: US 7,311,727 B2
(45) Date of Patent: Dec. 25, 2007

(54) ENCASED STENT

(75) Inventors: Mark M. Mazumder, Little Rock, AR (US); Jawahar L. Mehta, Little Rock, AR (US); Malay K. Mazumder, Little Rock, AR (US); Nawab Ali, Little Rock, AR (US); Steven Trigwell, Merritt Island, FL (US); Rajesh Sharma, Little Rock, AR (US); Samiran De, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 858 days.

(21) Appl. No.: 10/771,647

(22) Filed: Feb. 4, 2004

(65) Prior Publication Data

US 2004/0225346 A1   Nov. 11, 2004

Related U.S. Application Data

(60) Provisional application No. 60/445,033, filed on Feb. 5, 2003.

(51) Int. Cl.
*A61F 2/06* (2006.01)

(52) U.S. Cl. .................................. 623/1.44

(58) Field of Classification Search ........ 623/1.4–1.48; 606/198; 424/364, 411; 426/426; 427/2.24–2.25, 427/489
See application file for complete search history.

(56) References Cited

U.S. PATENT DOCUMENTS

| | | |
|---|---|---|
| 5,336,615 A | 8/1994 | Bell et al. |
| 5,516,781 A | 5/1996 | Morris et al. |
| 5,545,208 A | 8/1996 | Wolff et al. |
| 5,714,359 A | 2/1998 | Bowlin et al. |
| 5,797,887 A | 8/1998 | Rosen et al. |
| 5,851,231 A | 12/1998 | Wolff et al. |
| 5,957,972 A | 9/1999 | Williams et al. |
| 5,997,468 A | 12/1999 | Wolff et al. |
| 5,997,564 A | 12/1999 | Shehata et al. |

(Continued)

OTHER PUBLICATIONS

News Article, Author Unknown, Cilostazol Effectively Prevents Restenosis After Coronary Artery Stenting, Am Heart J, 2001, 141:124-130, 1 page printed from website http://cardiology.medscape.com on Feb. 22, 2001.

(Continued)

*Primary Examiner*—Vy Q. Bui
(74) *Attorney, Agent, or Firm*—Ray F. Cox, Jr.

(57) ABSTRACT

An encased stent that discourages restenosis by having a homogenous endothelial cell lining along the inner wall of the stent. The endothelial cell lining may be coated on the stent before the stent is placed in the artery, or the endothelial cell lining may be grown after placement by several factors that encourage such growth and discourage restenosis. The endothelial cells to coat the stent may be genetically modified to enhance the growth of the endothelial cells into a homogeneous lining. The stent has a continuous lining in the form of a multi-layer polymer coating, including a conducting biocorrosion inhibiting layer and a continuous film of polyurethane coupled by a coupling agent to polyethylene glycol. Various drugs and cell factors may be incorporated into the lining, such as anti-thrombin, anti-inflammatory and anti-coagulant drugs, cell cycle inhibitors, and vascular endothelial growth factors.

8 Claims, 27 Drawing Sheets

U.S. PATENT DOCUMENTS

| | | | |
|---|---|---|---|
| 6,099,562 | A | 8/2000 | Ding et al. |
| 6,117,166 | A | 9/2000 | Winston et al. |
| 6,206,914 | B1 | 3/2001 | Soykan et al. |
| 6,231,600 | B1 | 5/2001 | Zhong |
| 6,262,107 | B1 | 7/2001 | Li et al. |
| 2001/0000802 | A1 | 5/2001 | Soykan et al. |
| 2001/0044651 | A1 | 11/2001 | Steinke et al. |
| 2002/0049495 | A1 | 4/2002 | Kutryk et al. |
| 2002/0082689 | A1 | 6/2002 | Chinn |
| 2002/0086896 | A1 | 7/2002 | Kunz et al. |
| 2002/0090725 | A1 | 7/2002 | Simpson et al. |
| 2002/0091160 | A1 | 7/2002 | Cooke et al. |
| 2002/0102560 | A1 | 8/2002 | Pecker et al. |
| 2002/0133224 | A1 | 9/2002 | Bajgar et al. |
| 2003/0093141 | A1 | 5/2003 | Dimatteo et al. |
| 2003/0129214 | A1* | 7/2003 | Bornstein et al. ........... 424/423 |

OTHER PUBLICATIONS

Abstract, Severini, A., et al. Polyurethane-coated, self-expandable biliary stent: an experimental study, Acad Radiol, Dec. 1995; 2(12): 1078-81, PubMed, www.ncbi.nlm.nih,gov, 2 pages.

Website, www.stsduotek.com, Device Coatings, Technical Bulletin 6, STS duoTEK Inc., Copyright date 1997-2001, 3 pages.

Abstract, Isotalo, T., et al., Cytotoxicity Testing of a New Caprolactone-coated Self-expanding Bioabsorbable Self-Reinforced Poly-L-lactic Acid Urethral Stent, Urological Research, Apr. 1999; 27(2): 149-52, 1 page printed from PubMed, www.ncbi.nlm.nih.gov.

Abstract, Severini, A., et al., Polyurethane-coated, Self-expandable Biliary Stent: An Experimental Study, Acad Radiol, Dec. 1995, 2(12): 1078-81, 2 pages printed from PubMed, www.ncbi.nlm.nih.gov.

Abstract, Reid G., et al., Oral Flouroquinonolone Therapy Results in Drug Absorption on Urethral Stents and Prevention of Biofilm Formation, Int J Antimicrob Agents, Apr. 2001, 17(4): 317-9, 2 pages printed from PubMed, www.ncbi.nlm.nih.gov.

Reuters Medical News, Radioactive Stents Appear to Only Postpone Restenosis, 2 pages printed from website, http://cardiology.medscape.com, report from Circulation 2001; 103: 14-17.

Reuters Medical News, Neuotrophils May Play Role in Post-Angioplasty Restenosis, Arterioscler Thromb Vasc Biol 2000, 20: 2553-2558, 2 pages printed from website, http://cardiology.medscape.com.

Palmaz, J., Clinical Commentary, Stent Technology: Understanding Molecular Characteristics is Critical, Medscape Radiology 2001, 3 pages printed from website http://cardiology.medscape.com on Apr. 16, 2001.

Abstract, Rogers, C., et al., Endovascular Stent Design Dictates Experimental Restenosis and Thrombosis, *Circulation*, 1995; 91: 2995-3001, 3 pages printed from website http://circ.ahajournals.org.

Website, www.jnj.com, Cordis Introduces Bx Velocity™ 'HEPACOAT™' Stent—Heparin-Coated Care for Coronary Artery Disease, Johnson & Johnson, Nov. 14, 2000, 3 pages.

Uretsky, B., et al., A Prospective Evaluation of Angiography-Guided Coronary Stent Implementation with High Versus Very Balloon Inflation Pressure, American Heart Journal, 140(5): 804-12, Nov. 2000.

Rechavia, E., et al., Biocompatibility of Polyurethans-Coated Stents: Tissue and Vascular Aspects., *Catheterization and Cardiovascular Diagnosis*, 45(2): 202-207, Wiley-Liss, Inc. 1998.

Trigwell, S., et al., Effects of Surface Treatment on the Surface Chemistry of NiTi Alloy for Biomedical Applications, *Surface and Interface Analysis*, 26: 483-489, John Wiley & Sons, Ltd., 1998.

Trepanier, C., et al., Effect of Modification of Oxide Layer on NiTi Stent Corrosion Resistance, Journal of Biomedical Materials Research Part B: Applied Biomaterials 43 (4) 433-440, John Wiley & Sons, Inc., 1998, published online Jan. 7, 1999.

Rondelli, B., et al., The Corrosion Behavior of Nickel Titanium Shape Memory Alloys, *Corrosion Science*, vol. 30, No. 8/9, pp. 805-812, Pergamon Press, 1990.

News Article, Author Unknown, Type of Stent a Critical Factor in Coronary Artery Restenosis, Am J Cardiol, 2001, 87:34-39, 1 page printed from website http://cardiology.medscape.com on Jan. 23, 2001.

Schellhammer, F., et al., Preliminary Report. Poly-Lactic-Acid Coating for Endovascular Stents. Preliminary Results in Canine Experimental Arteriovenous Fistulae, *Investigative Radiology*, vol. 32, No. 3, Mar. 1997, pp. 180-186.

Dai, K. et al., Studies and Applications of NiTi Shape Memory Alloys in the Medical Field in China, Bio-Medical Materials and Enginering, 6 (1996), pp. 233-240, IOS Press.

Williams, D., On the Biocompatibility of High Technology Materials, Materials Research Society Symposium Proceedings vol. 55, Materials Research Society, 1986, pp. 117-126.

Roguin, A., et al., The Acute Effect of Stenting with the Nitinol Self-Expanding Coil Stent: Preliminary Experience, International Journal of Cardiac Imaging, 13, Kluwer Academic Publishers, Dec. 1997, pp. 441-450.

Trepanier, C., et al., Preliminary Investigation of the Effects of Surface Treatments on Biological Response to Shape Memory NiTi Stents, J Biomed Mater Res 48: 165-171, John Wiley & Sons, Inc., 1999.

Schellhammer, F., et al., Polyethylene Terephthalate and Polyurethane Coatings for Endovascular Stents: Preliminary Results in Canine Experimental Arteriovenous Fistulas, Radiology, vol. 211, No. 1, pp. 169-175, 1999.

Shabalovskaya, S., et al., Surface Spectroscopic Characterization of TiNi Nearly Equiatomic Shape Memory Alloy for Implants, J. Vac. Sci. Technol. A 13(5), American Vacuum Society, Sep./Oct. 1995, pp. 2624-2632.

Gibbons, D., What Can We Predict Before It's Implanted?, Materials Research Society Symposium Proceedings vol. 55, Materials Research Society 1986, pp. 139-150.

Abstract, Henry , M., et al., Initial Experience with the Cragg Endopro System 1 for Intraluminal Treatment of Peripheral Vascular Disease, J Endovasc Surg, Sep. 1994, p. 31-43, 2 pages printed from website oclc.org.

Press Release, Implant Sciences Corporation and Cardiotech International Announce Development of Drug-Eluting Stent, Implant Sciences Corporation, Wakefield and Woburn MA, Aug. 29, 2001, printed from website www.implantsciences.com/cn/pr/2001/pr_01aug29.html.

Kim, D., et al. Evaluation of the Biodurability of Polyurethane-Covered Stent Using a Flow Phantom, Korean J Radiol 2(2), 75-79, Jun. 2001.

Ryhanen, J. Abstract, Biocompatibility evaluation of nickel-titanium shape memory metal alloy, University of Oulu, Oulu, Finland, 1999, 2 pages printed from website http://herkules.oulu.fi.

Oshida, Y., et al., Corrosion and Biocompatibility of Shape Memory Alloys, Corrosion Engineering, 40(12), pp. 1009-1025, 1991.

Brigouri, C., et al., Emergency Polytetrafluorethylene-Covered Stent Implantation to Treat Coronary Ruptures, Circulation 102, 3028-3031, Dec. 19/26, 2000.

Scheerder, I., et al., Experimental Study of Thrombogenicity and Foreign Body Reaction Induced by Heparin-Coated Coronary Stents, Circulation, Mar. 18, 1997; 95:1549-1553.

Author Unknown, Shape Memory Effect, 2 pages printed from website www.aem.umn.edu on Jan 20, 2000.

Abstract, Sheth, S., et al., Subacute Thrombosis and Vascular Injury Resulting from Slotted-Tube Nitinol and Stainless Steel Stents in a Rabbit Carotid Artery Model, Circulation, 1996; 94:1733-1740, 2 pages printed from website http://circ.ahajournals.org.

New Article, Author Unknown, Sirolemus-Coated Stents Reduce Coronary Angioplasty Restenosis Rates, 1 page reprinted from http://cardiology.medscape.com on Jan. 19, 2001.

Abstract, Verheye, S., et al., Reduced Thrombus Formation by Hyaluronic Acid Coating of Endovascular Devices, Arteriosclerosis, Thrombosis, and Vascular Biology, 2000; 20:1168, 2 pages printed from website http://atvb.ahajournals.org.

Abstract, Alt, E., et al., Inhibition of Neointima Formation After Experimental Coronary Artery Stenting, Circulation, 2000; 101:1453, 2 pages printed from website http://circ.ahajournals.org.

Abstract, Albiero, R., et al., Edge Restenosis After Implantation of High Activity $^{32}$P Radioactive β-Emitting Stents, Circulation, 2000; 101:2454, 2 pages printed from website http://circ.ahajournals.org.

Abstract, Tamai, H., Initial and 6-Month Results of Biodegradable Poly-I-Lactic Acid Coronary Stents in Humans, Circulation, 2000; 102:399, 2 pages printed from website http://circ.ahajournals.org.

Abstract, Aggarwal, R., et al., Antithrombotic Potential of Polymer-Coated Stents Eluting PlateletGlycoprotein llb/llla Receptor Antibody, Circulation, 1996; 94:3311-3317, 2 pages printed from website http://circ.ahajournals.org.

News Article, Author Unknown, Radiation May Provide a New Ray of Hope for an Old Problem, Jan. 31, 2000, 2 pages printed from website http://cardiology.medscape.com.

Abstact, Carter, A., et al., Effects of Endovascular Radiation from a β-Particle-Emitting Stent in a Porcine Coronary Restenosis Model, Circulation, 1996; 94:2364-2368, 2 pages printed from website http://circ.ahajournals.org.

Abstract, Kastrati, A, et al., Increased Risk of Restenosis After Placement of Gold-Coated Stents, Circulation, 2000; 101:2478, 2 pages printed from website http://circ.ahajournals.org.

Hoffman, R., et al., Patterns and Mechanisms of In-Stent Restenosis, Circulation, 1996: 94:1247-1254, 16 pages printed from website http://circ.ahajournals.org.

Author Unknown, Biocompatibility Evaluation of Nickel-Titanium Shape Memory Metal Alloy, Chap. 2 Review of the Literature, 2.8 Biocompatibility of NiTi, 15 pages printed from website http://herkules.oulu.fi on Feb. 19, 2001.

Author Unknown, Biocompatibility Evaluation of Nickel-Titanium Shape Memory Metal Alloy, Chap. 4 Materials and Methods, 4.1 Test Implants, 2 pages printed from website http://herkules.oulu.fi on Feb. 19, 2001, Copyright date 2000, Oulu University Library.

Author Unknown, Biocompatibility Evaluation of Nickel-Titanium Shape Memory Metal Alloy, Chap. 4 Materials and Methods, 4.2 In Vitro Human Cell Cultures, 2 pages printed from website http://herkules.oulu.fi on Feb. 19, 2001, Copyright Date 2000, Oulu University Library.

Author Unknown, Biocompatibility Evaluation of Nickel-Titanium Shape Memory Metal Alloy, Chap. 5 Results, 5.1 Cell Attachment and Proliferation in the Presence of NiTi, 7 pages printed from website http://herkules.oulu.fi on Feb. 19, 2001, Copyright Date 2000, Oulu University Library.

Author Unknown, Biocompatibility Evaluation of Nickel-Titanium Shape Memory Metal Alloy, Chap. 6, 6.1 Cell Proliferation and Connection with NiTi in Vitro, 1 page printed from website http://herkules.oulu.fi on Feb. 19, 2001.

Author Unknown, Biocompatibility Evaluation of Nickel-Titanium Shape Memory Metal Alloy, Chap. 7 Conclusion, 2 pages printed from website http://herkules.oulu.fi on Feb. 19, 2001, Copyright Date 2000, Oulu University Library.

Szycher, M., et al. Drug-Eluting Stents to Prevent Coronary Restenosis, CardioTech International, Inc., Woburn Massachusetts, Implant Sciences Corporation, Wakefield Massachusetts, 2002, 10 pages, www.implantsciences.com/pdf/IMXpaperv2-rev2.pdf.

Kleshinski, S., et al., Medical Stenting: A Synthesis of Design Principles, SMST-97: Proceedings of the Second International Conference on Shape Memory and Superelastic Technologies, Pacific Grove CA, 1997, pp. 561-565.

* cited by examiner

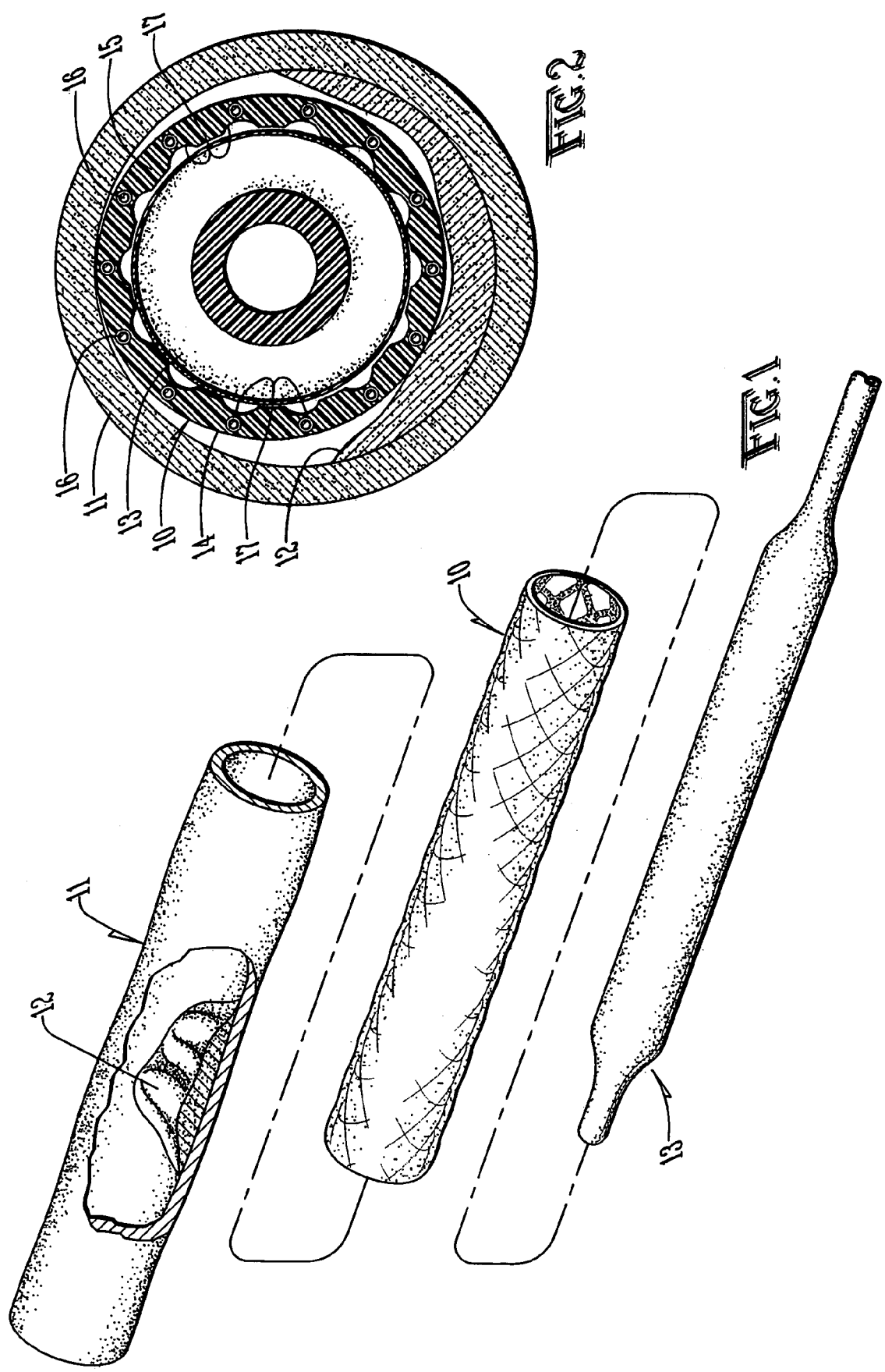

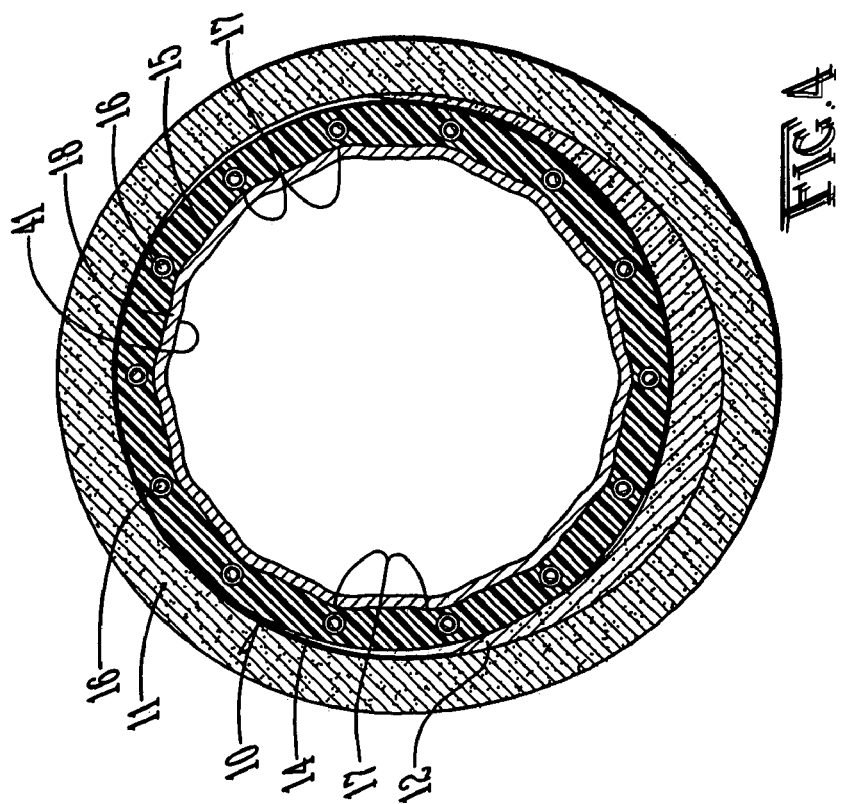
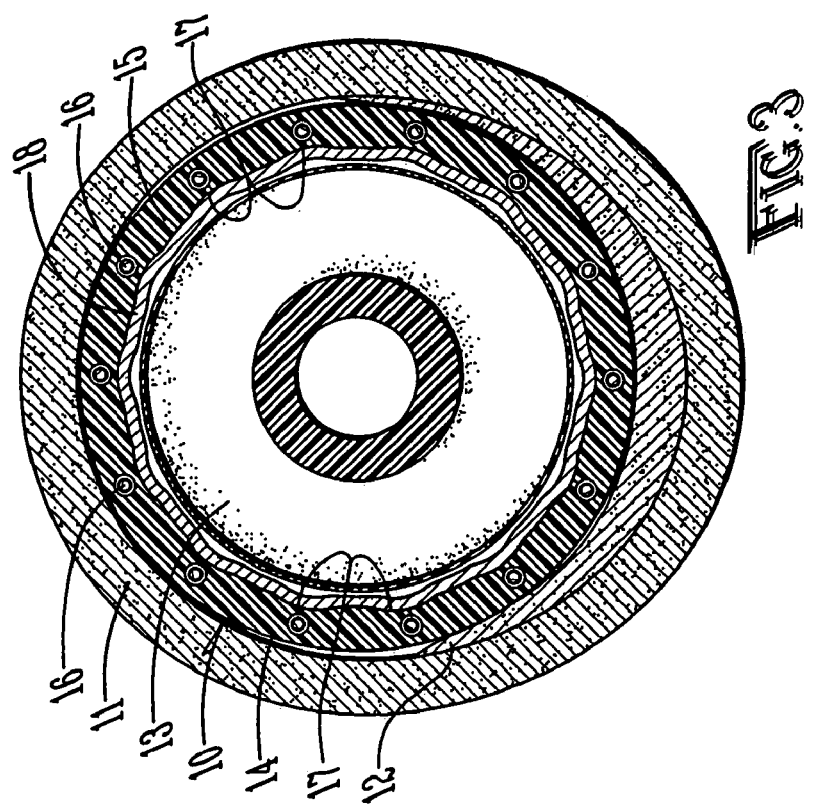

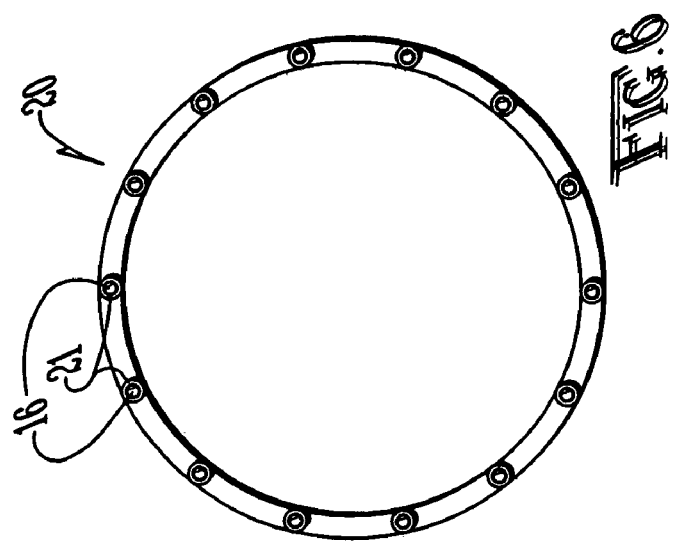
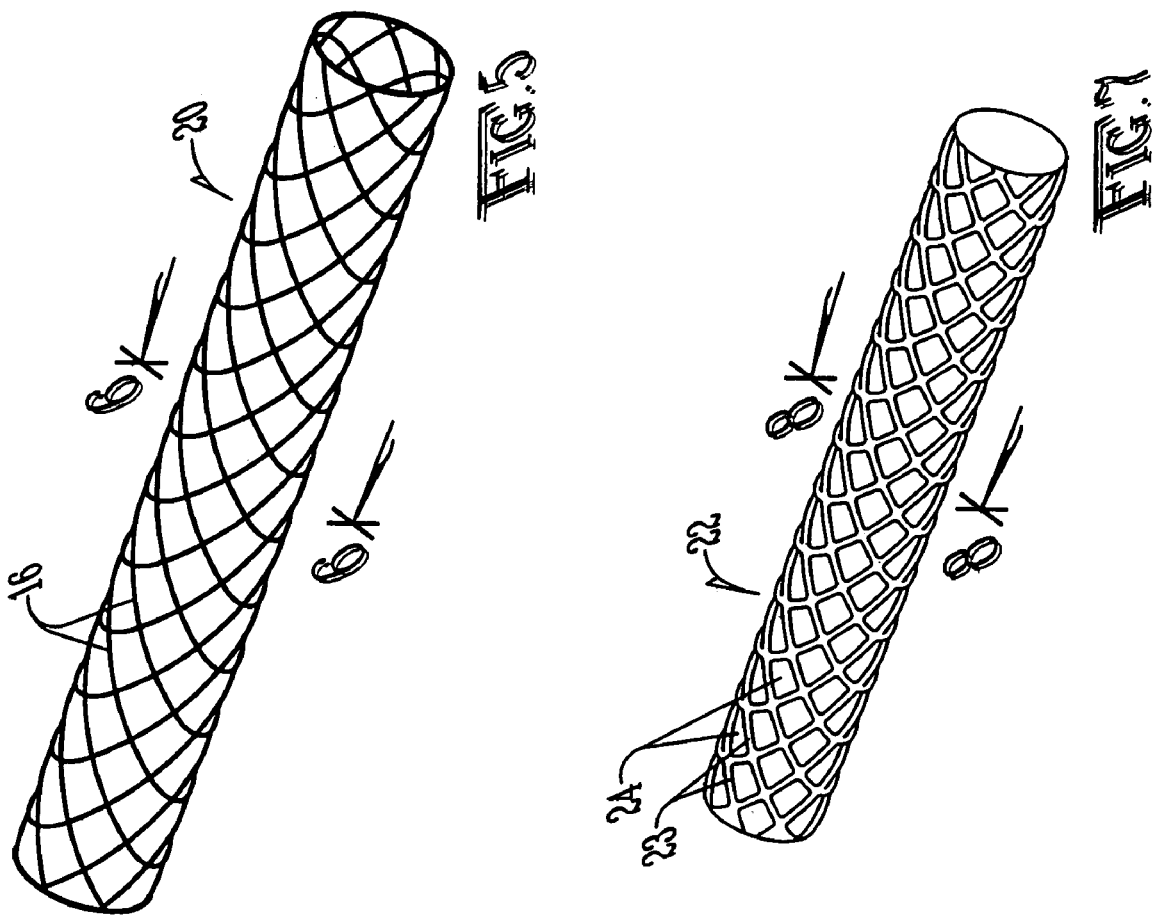

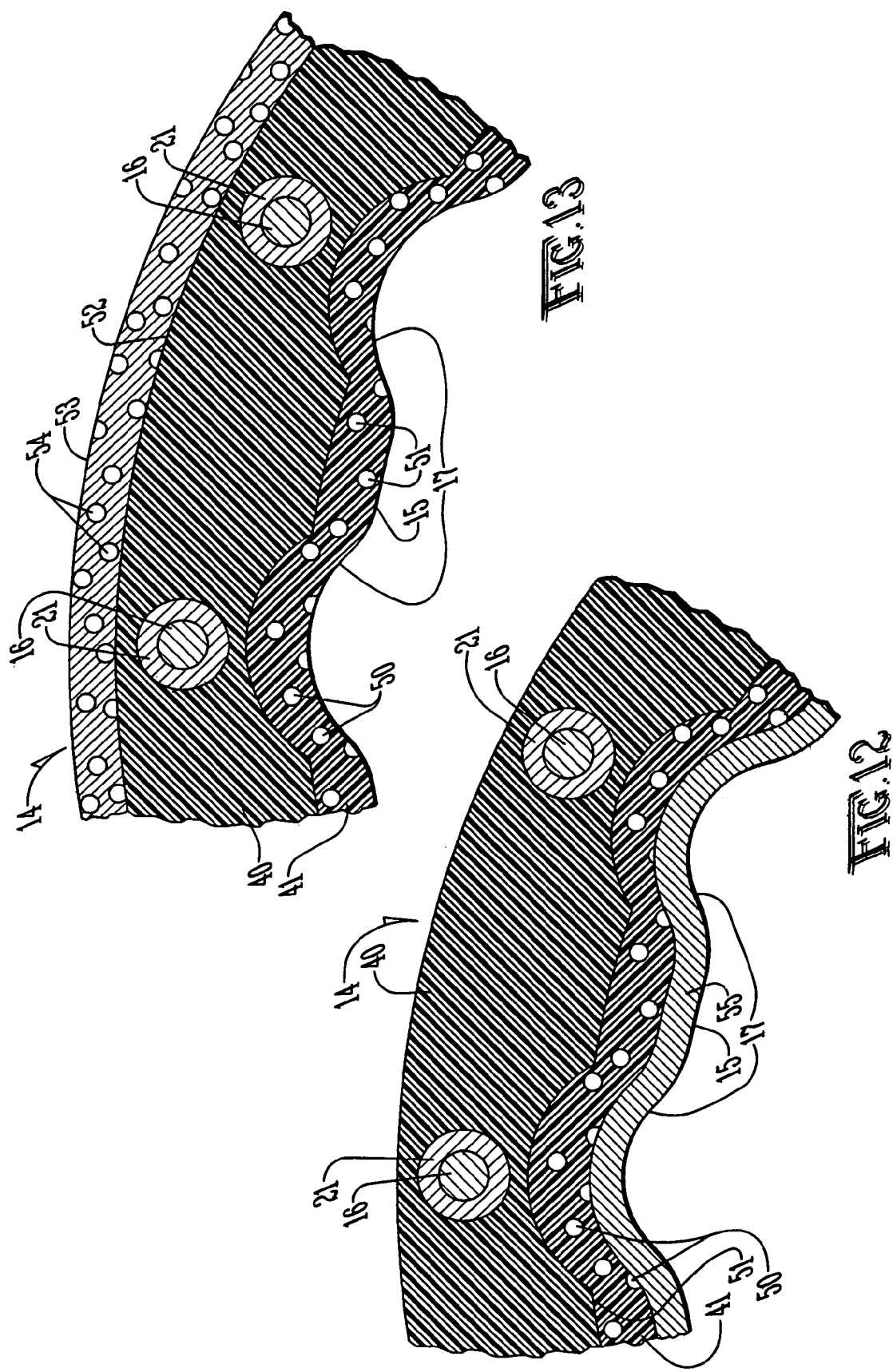

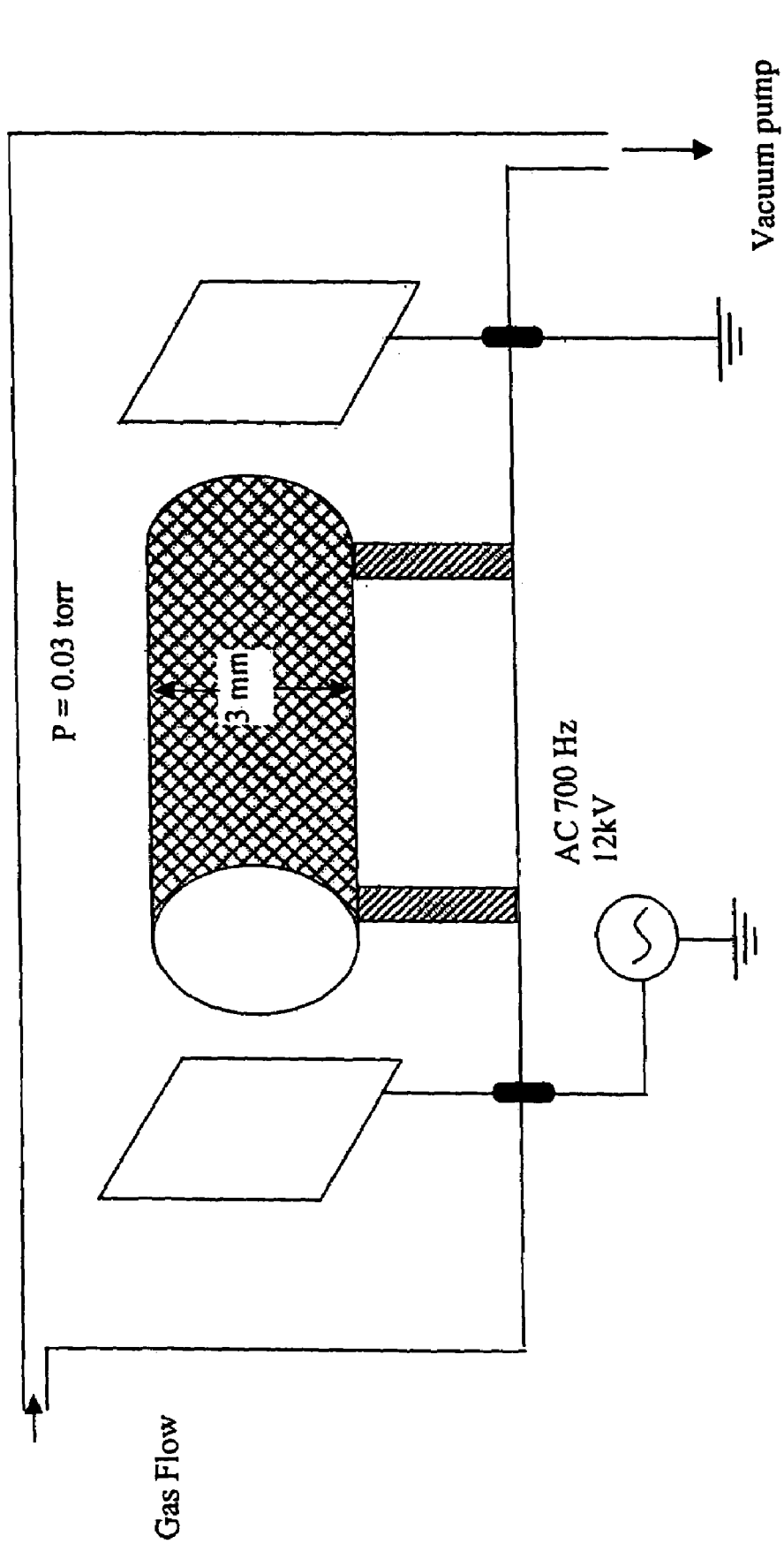
Fig. 16 A. Low-pressure plasma reactor for surface modification of stent metal mesh

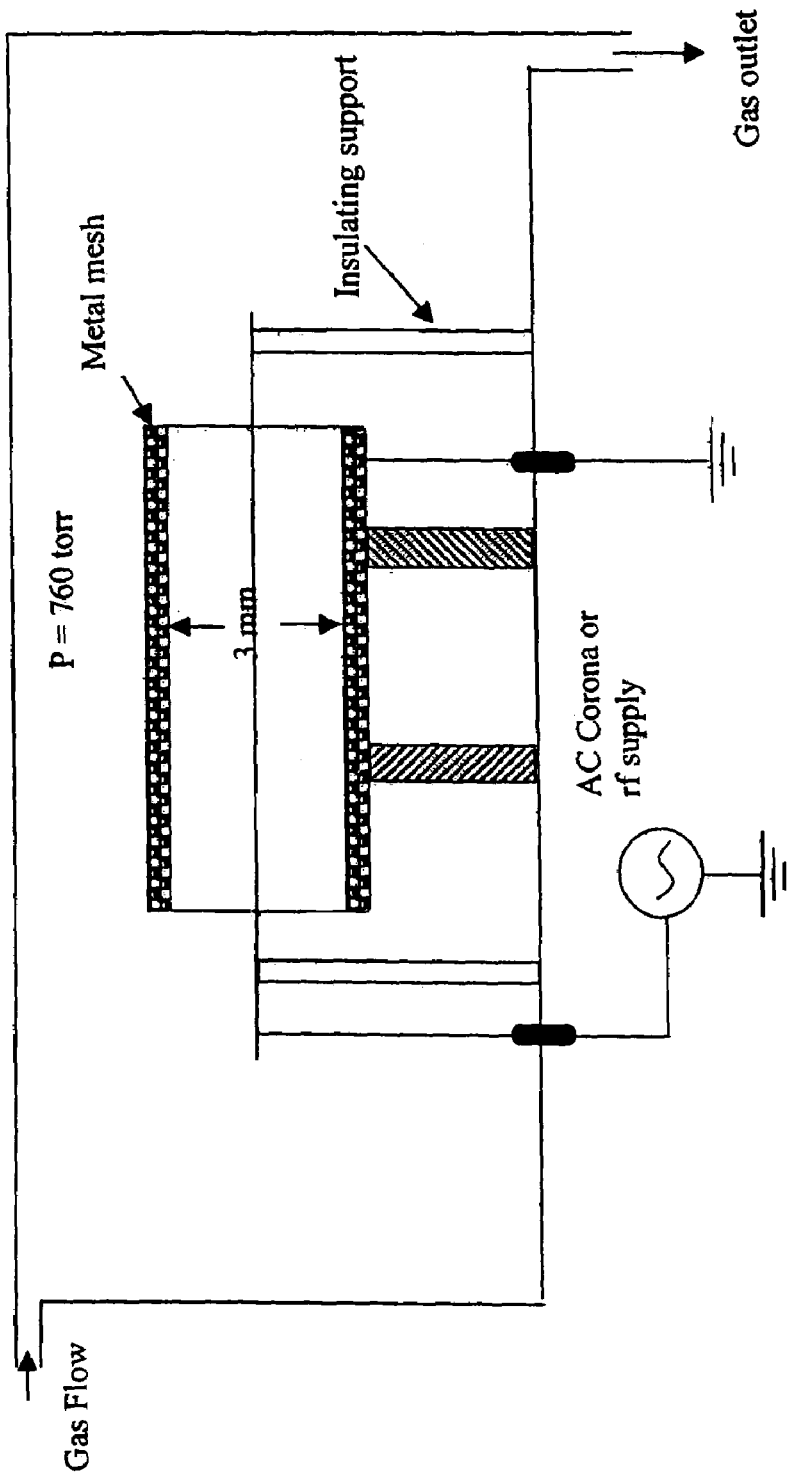
Fig. 16 B. Atmospheric pressure plasma reactor for surface modification of inner lining of polyurethane encased stent

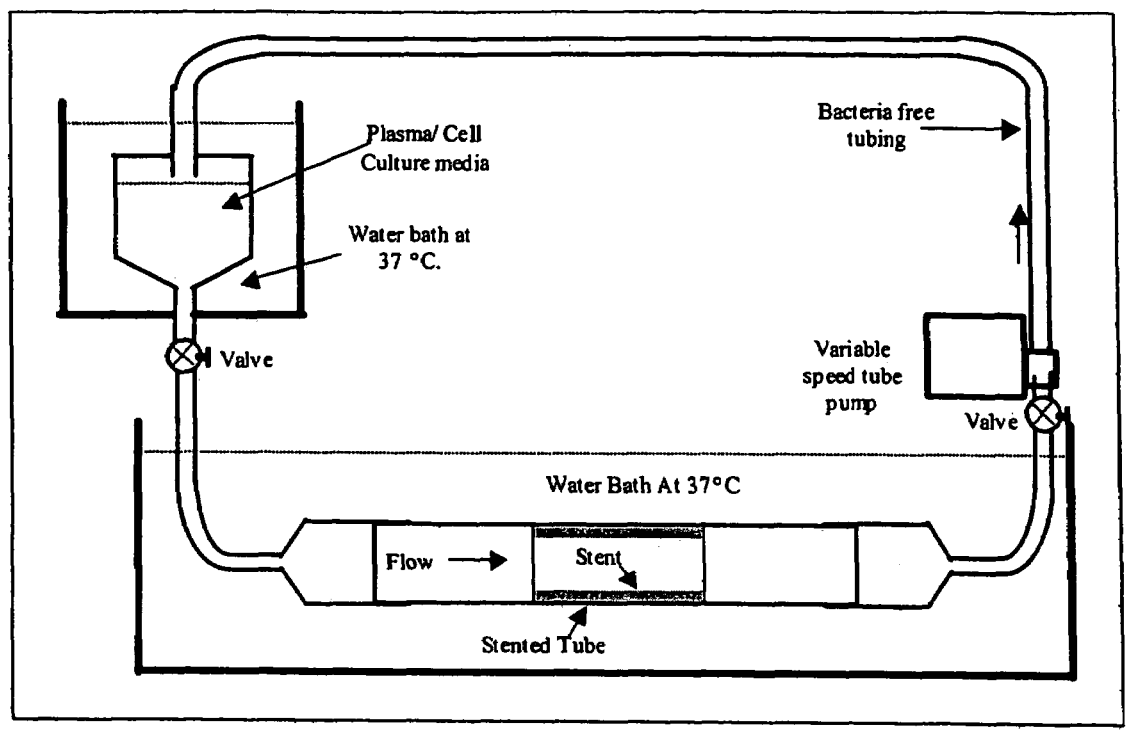
Figure 17: Flow Cell for Endothelial Cell Growth Studies

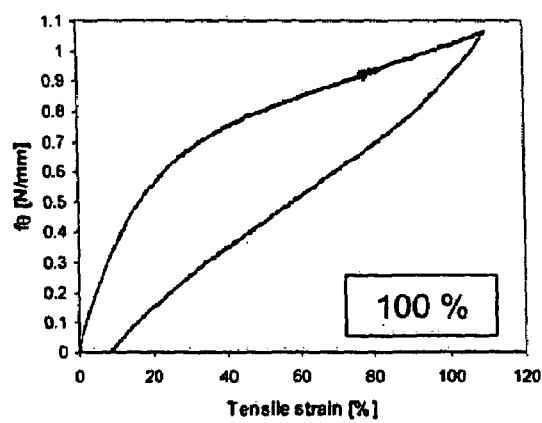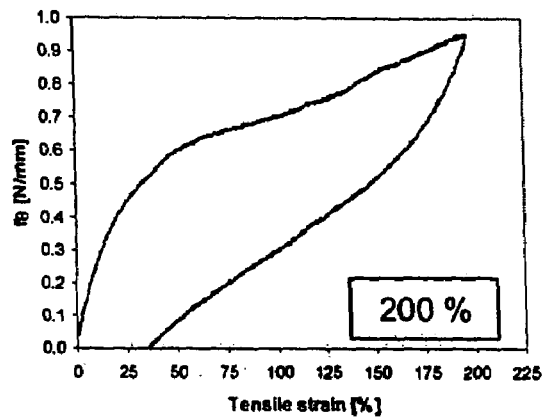
Fig. 20A                    Fig. 20B

Functional group atomic concentration [%]

Fig. 26A
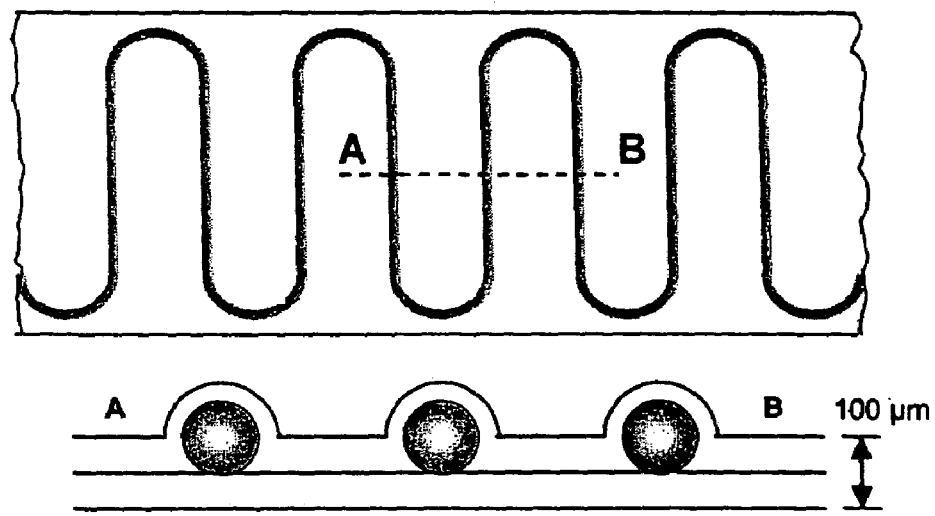
Fig. 26B
Fig. 27A 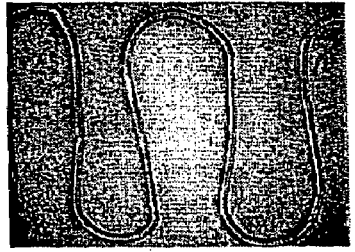 Fig. 27B 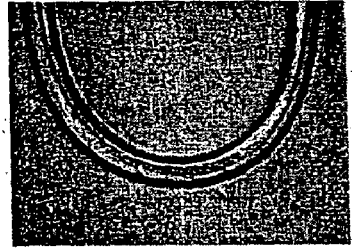 Fig. 27C 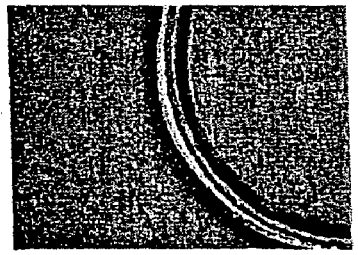
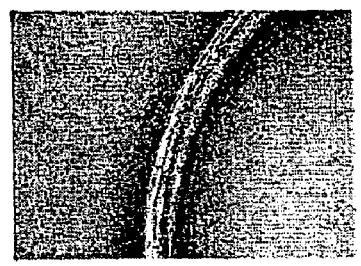 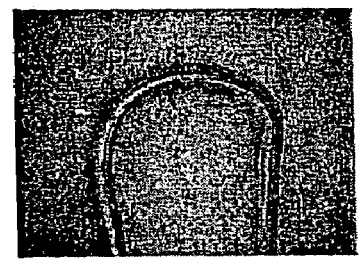 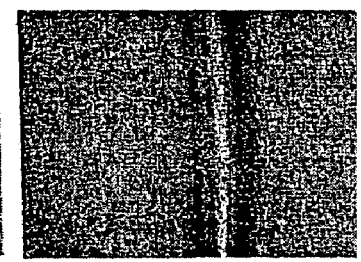
Fig. 27D · Fig. 27E · Fig. 27F

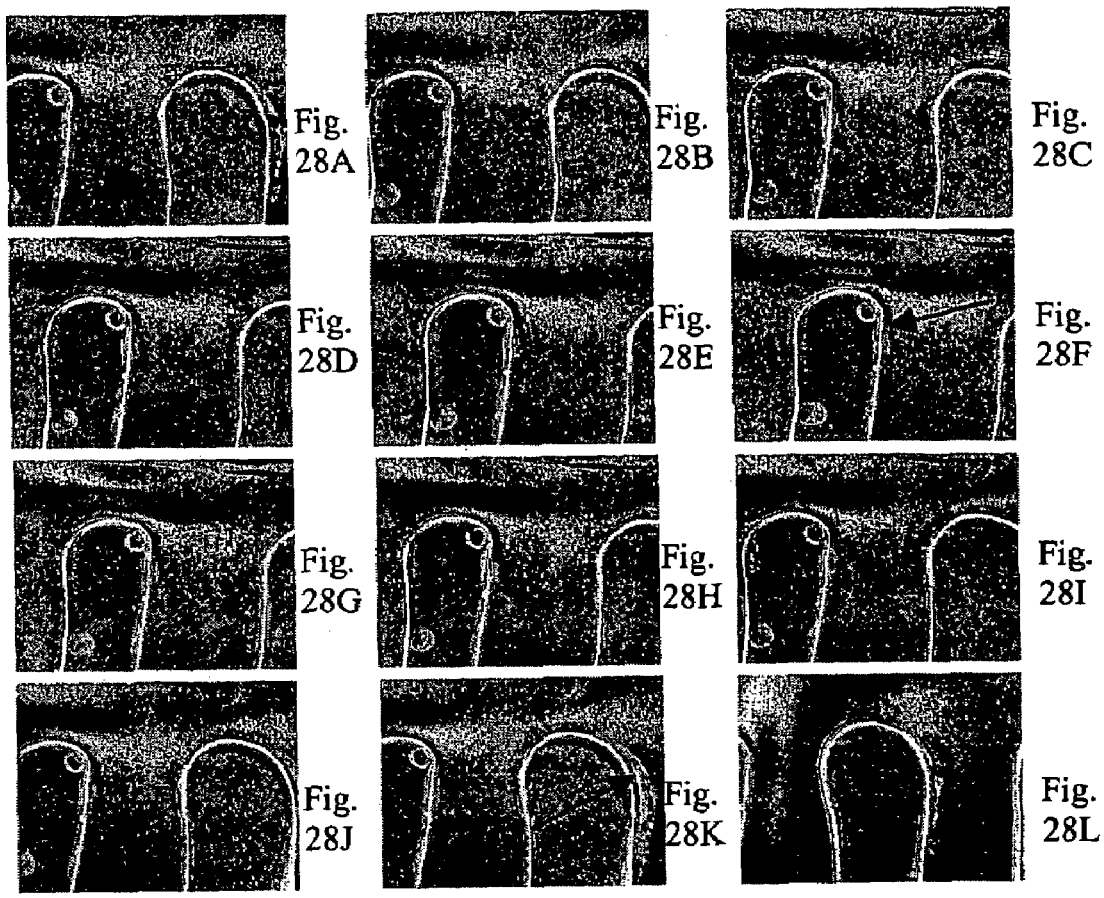
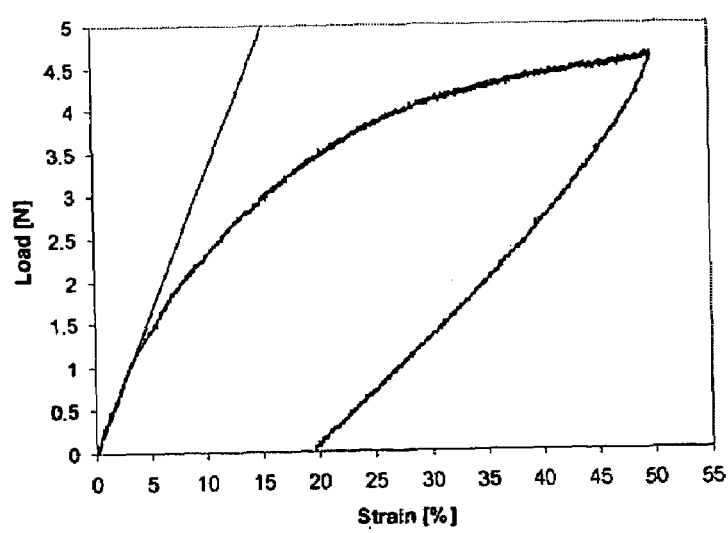
Fig. 29

Fig. 32A
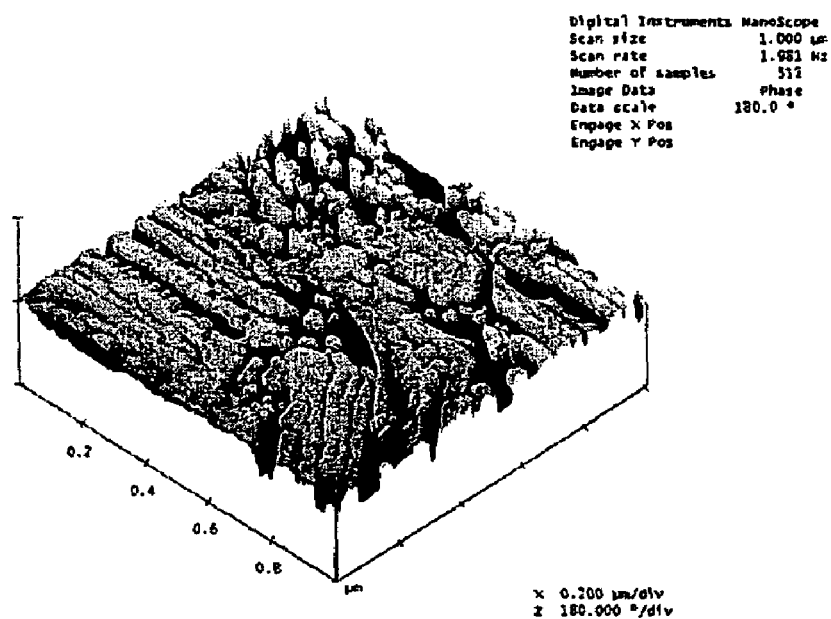
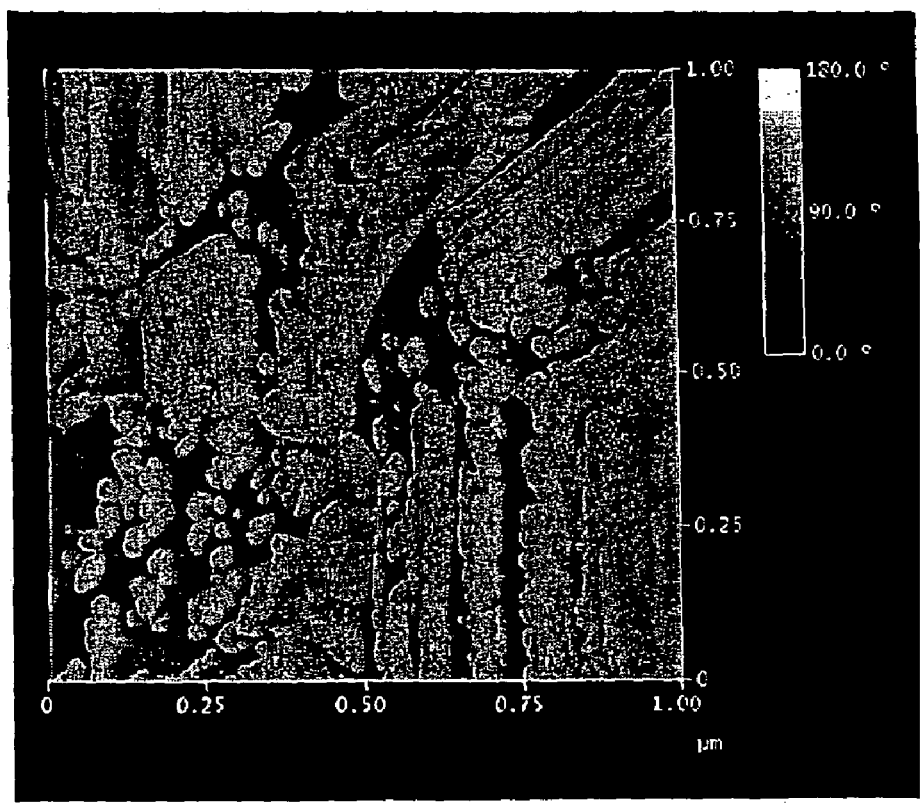
Fig. 32B

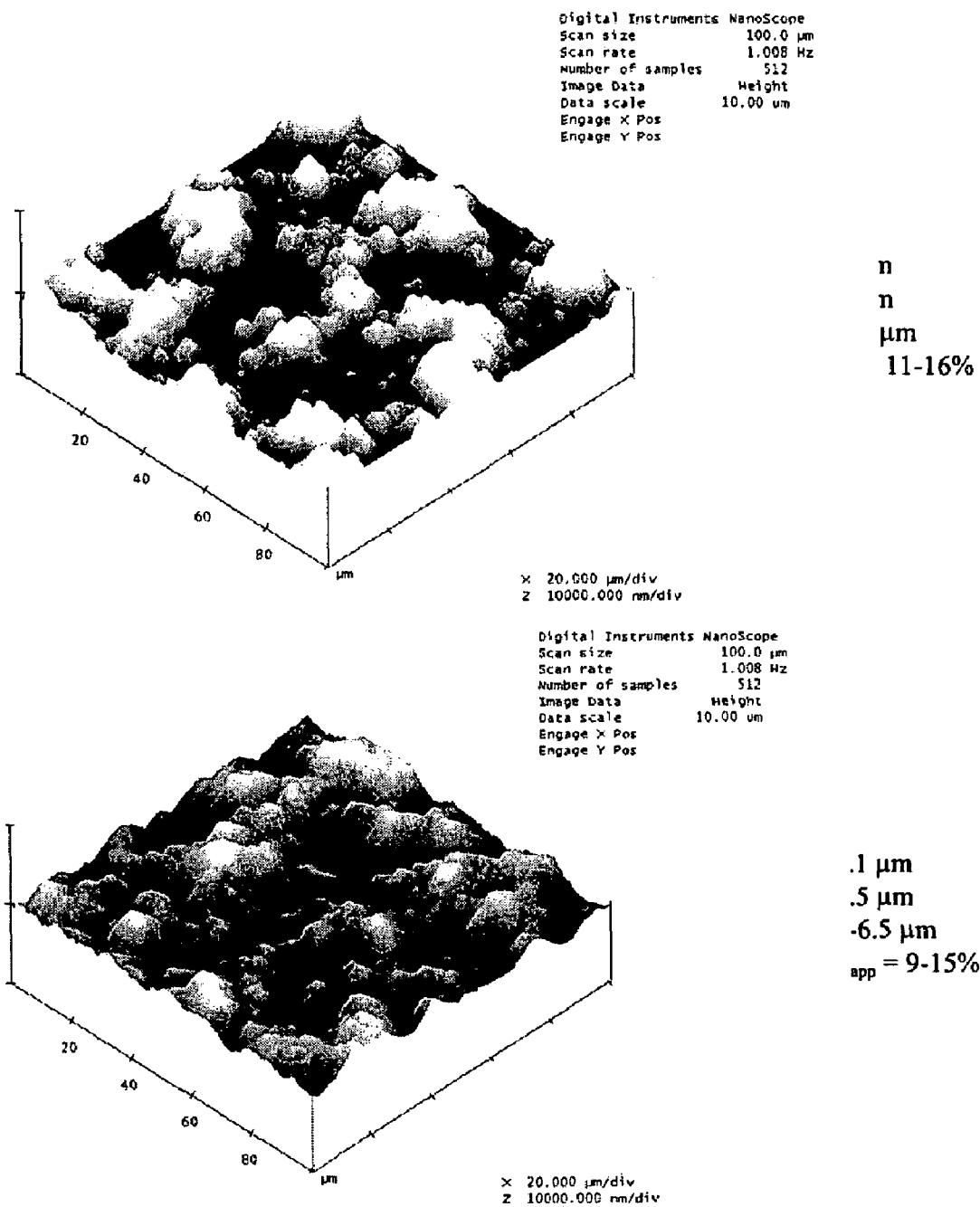

Fig. 35A
Fig. 35B
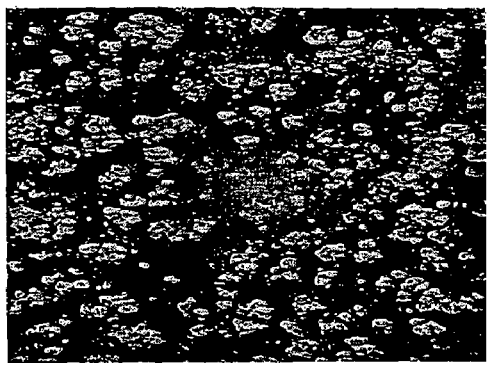
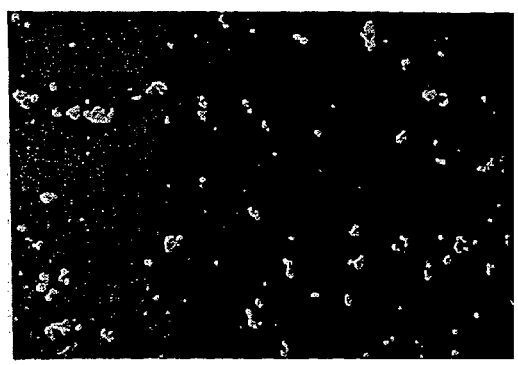

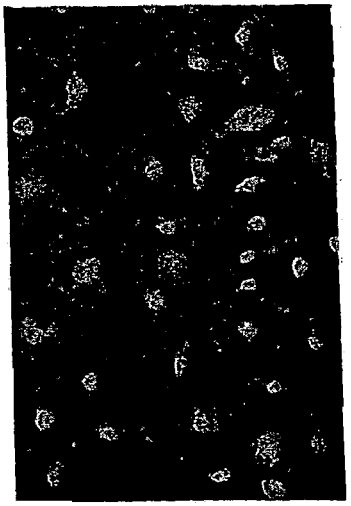
Fig. 37A  Fig. 37B  Fig. 37C
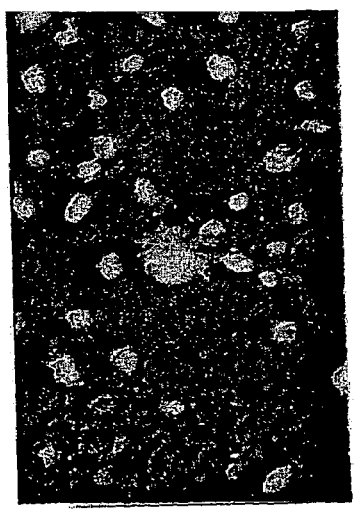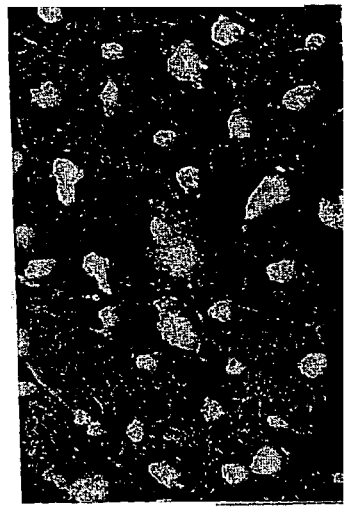
Fig. 38A  Fig. 38B  Fig. 38C

ENCASED STENT

CROSS-REFERENCE TO RELATED APPLICATIONS

This application claims the benefit of U.S. Provisional Application No. 60/445,033 filed Feb. 5, 2003, which is incorporated herein by reference.

STATEMENT REGARDING FEDERALLY SPONSORED RESEARCH OR DEVELOPMENT

Not applicable.

BACKGROUND OF THE INVENTION

1. Field of the Invention

The present invention relates to an implantable medical device, and in particular, to a vascular stent having a continuous coating to encourage the growth of an endothelial cell layer for discouraging restenosis.

2. Brief Description of the Related Art

Narrowing of the arteries (stenosis) may be treated by balloon angioplasty, where a balloon is inflated in the blocked segment of the artery to stretch the artery and flatten the obstruction in order to increase blood flow. Angioplastied arteries may experience a re-narrowing after angioplasty (a process called restenosis). One method of treatment to prevent restenosis is to mechanically hold the artery open with a stent.

A stent is typically an open mesh cylindrical device which fits into the opened artery and expands radially against the walls of the artery. There are two types of stents: 1) balloon expandable stents made of stainless steel mesh and 2) self-expanding (temperature sensitive) stents with a high elasticity, composed of "smart metals". While most stents are made of type 316 Stainless Steel (SS), there is a recent trend towards using stents made of shape memory alloys containing nickel and titanium (Nitinol). Shape Memory Alloys (SMAs) refer to alloys that retain their original shape when exposed to a certain temperature threshold. These stents are designed to contract or contort under a cold environment and expand or return to their original shape under warm temperatures.

Stents using SMAs contain 55% nickel and 45% titanium and expand automatically at the body temperature of 37° C. to apply a constant radial pressure against the arterial wall, preventing its collapse. Unlike stainless steel stents, which require angioplastic balloon pressure to expand, nitinol stents expand independently. However, nickel is toxic and leaches out over a prolonged period of time. Therefore, nitinol stents require a suitable coating.

While a stent may be effective in preventing restenosis, restenosis can nevertheless occur. Various factors may contribute to restenosis. For example, the stented site may reocclude due to intense coagulation reaction at the stented site. The proliferation of vascular smooth muscle cells over and through the stent may contribute to restenosis.

Current stent research is focused on creating biocompatible stents that remain effective for a long period of time without requiring a second stenting procedure within the affected lumen. Most research focuses on coating the stents with antithrombogenic drugs to prevent platelet aggregation. This approach only shows promise for the short-term delay of restenosis. As the drugs undergo dissolution within the bloodstream, their effectiveness is reduced.

One solution that is occasionally implemented is to insert beta-particle-emitting radioactive drugs or chemicals into the stent to prevent restenosis from occurring. Such a solution is a compromise between the possibility of cancer caused by radiation and the possibility of restenosis caused by a local vascular tissue reaction.

The following describes various attempts that have been made to develop stents that are coated with substances that discourage restenosis.

For example, U.S. Pat. No. 6,231,600 to Zhong discloses a stent with a multilayer coating. In particular, a first layer of polymer such as a polyurethane, including restenosis-inhibiting substances such as paclitaxel, is coupled by a crosslinking agent to a second non-thrombogenic layer. The crosslinking agent is preferably a polyfunctional aziridine and the second layer includes heparin.

U.S. Pat. No. 6,206,914 to Soykan et al. discloses a stent carrying eukaryotic cells, including genetically-engineered endothelial cells, capable of producing and releasing a therapeutic agent. Furthermore, the stent includes a polymer coating covering at least a portion of either the exposed or the wall-contacting surface of the stent. The polymer film may also incorporate anti-thrombogenic or anti-inflammatory agents.

Published U.S. patent application No. 2002/0049495 discloses a stent coated with a polymer such as polyurethane or polyethylene glycol. The polymer incorporates antibodies which promote endothelial cell growth. The endothelial cells may be added to the coated stent before implantation or may grow onto the stent after implantation. The endothelial cells may be genetically modified. The antibodies may be tethered to the polymer layer by linking molecules.

Published U.S. patent application No. 2002/0102560 and U.S. Pat. No. 5,957,972 both disclose genetically modified endothelial cells that may be used to coat stents to prevent restenosis.

Various drugs and cell factors have been suggested to treat restenosis. For example, U.S. Pat. No. 5,516,781 is directed to the treatment of restenosis with rapamycin. U.S. Pat. No. 6,231,600 discloses a stent with a hybrid coating incorporating paclitaxel.

A stent coating must be resistant to 1) bacterial infection, 2) cellular inflammation, 3) a foreign body reaction, 4) platelet aggregation, and 5) corrosion. Polymer coating of implants for improving biocompatibility has a proven efficacy. Some of the polymers used are polyurethane, polylactic acid, and polytetrafluroethylene (PTFE), which is known as Teflon®. The objective of polymer coating is to minimize the foreign-body reaction, which is an inflammatory response characterized by multinucleated giant cells engulfing the stents, platelet formation, and thrombogenesis. Previous studies have shown that polyurethane is one of the most biocompatible polymers; it is flexible, it can be formulated as a hydrophilic coating, and it is not cytotoxic. One type of polyurethane contains aromatic isocyanates. One of the most commonly used polyurethanes for coating is bis (4isocyanatophenyl) methane, also referred to as MDI. Previous studies have shown that hydrophilic polyurethane coatings of implants are one of the most useful and effective biocompatible coatings. Other known biocompatible polymers include polyester and the natural organic polymer, rubber.

BRIEF SUMMARY OF THE INVENTION

The present invention is a novel stent that discourages restenosis by having a homogenous endothelial cell lining along the inner surface of the stent. Such a cell lining prevents the conversion of fibrin to fibrinogen and the aggregation of platelets. The endothelial cell lining may be coated on the stent before the stent is placed in the artery, or the endothelial cell lining may be grown after placement by several factors that encourage such growth and discourage restenosis. The endothelial cells to coat the stent may be genetically modified to enhance the growth of the endothelial cells into a homogeneous lining.

In order to have a homogeneous endothelial cell lining, the stent must have a continuous film rather than a mesh. In the present invention, the stent (which may be formed from stainless steel, nitinol or other materials) has a multi-layer polymer coating. The stent are pretreated prior to applying the polymer coating. The pretreatment may include chemical etching. The pretreatment includes plasma etching to generate a thick passive oxide layer on the metal surface and improves corrosion resistance against biological fluids. The pretreatment also makes the surface microstructure rougher and improves adhesion of the polymer coating. To add the polymer coating, the stent wires are first coated with a conducting biocorrosion inhibiting layer (ligno-pani) to prolong the life of the stent. The stent is next coated with a continuous film of polymer which comprises polyurethane coupled by a coupling agent (toluene diiosocyanate) to polyethylene glycol. Various drugs and cell factors may be incorporated into the lining, such as anti-thrombin, anti-inflammatory and anti-coagulant drugs, cell cycle inhibitors, and vascular endothelial growth factors. The drugs could include a combination of one or more of the following: heparin/aspirin, rapamycin, cipro-floxacin, paclitaxel, diazeniumdiolate, iNOS and $Ca^{2+}$ influx, gene suppression drugs and clot-blocking drugs, such as ReoPro. The polyethylene glycol molecules are attached in such a way that they serve to slow the release of the drugs from the lining. While one set of drugs may be incorporated into the polymer layer on the inner surface of the stent, different drugs may be incorporated into a polymer layer the outer surface of the stent.

In one embodiment of the present invention, the polymer coating is a radially expandable cylindrical film which expands uniformly during balloon angioplasty. In another embodiment, the polymer coating is formed with a corrugated inner surface which when expanded has a circular cross-section opening the clogged artery. An advantage of the corrugated structure is that only a small fraction of the stent's inner wall is pressurized during expansion, therefore any endothelial cells used for seeding the stent will be preserved and will be effective for rapid growth of a lining on the inner wall of the stent. The circular encasement is easier to manufacture and can be expanded up to 225% of its initial diameter.

In order to allow the polymer coating to expand into a smooth homogeneous lining, a grooved wax core may be used in the manufacturing process. In the first step of the manufacturing process, the stent wires are coated with the biocorrosion inhibiting conductive polymer. A grooved wax core, whose diameter is selected to fit closely into the stent, is placed inside the stent. Next a thin film of polyurethane is applied to the stent. The wax core is removed. The grooves in the wax core produce a layer of polyurethane which varies in thickness so that the stent may be flexibly and uniformly expanded upon placement in the artery. The end result is a substantially smooth continuous coating to support the growth of a homogenous lining of endothelial cells. The coupling factor and the polyethylene glycol are added onto the polyurethane layer along with the drug and cell factors.

The inner wall of the encased stent is plasma treated for optimal wettability of the surface and for sterilization for supporting the growth of an endothelial cell lining.

The stent may be seeded with endothelial cells by using a flow cell under a simulated blood flow environment.

It is therefore an object of the present invention to provide for a novel stent that discourages restenosis by having a homogenous endothelial cell lining along the inner wall of the stent.

It is a further object of the present invention to provide for such a stent having a continuous lining in the form of a multi-layer polymer coating, including a conducting biocorrosion inhibiting layer and a continuous film of polyurethane coupled by a coupling agent to polyethylene glycol.

It is also an object of the present invention to provide such a stent wherein various drugs and cell factors are incorporated into the lining, such as anti-thrombin, anti-inflammatory and anti-coagulant drugs, cell cycle inhibitors, and vascular endothelial growth factors.

These and other features, objects and advantages of the present invention will become better understood from a consideration of the following detailed description of the preferred embodiments and appended claims in conjunction with the drawings as described following:

BRIEF DESCRIPTION OF THE SEVERAL VIEWS OF THE DRAWINGS

FIG. 1 is an exploded perspective view of the stent of the present invention as it would be inserted into an occluded artery using an angioplasty balloon.

FIG. 2 is a cross-section of the stent of FIG. 1 inserted into the occluded artery with the angioplasty balloon in position within the stent and before expansion of the balloon.

FIG. 3 is a cross-section of the stent of FIG. 2 showing the stent as it is expanded against the walls of the occluded artery as the angioplasty balloon is expanded.

FIG. 4 is a cross-section of the expanded stent of FIG. 3 after the angioplasty balloon is removed.

FIG. 5 is a perspective view of a wire mesh which forms the foundation of the encased stent of the present invention.

FIG. 6 is a cross-section view of the stent of FIG. 5 along the line 6-6 of FIG. 5. The wires forming the wire mesh have been coated with a corrosion inhibiting layer.

FIG. 7 is a perspective view of a knurled wax core for forming a stent encased in a continuous polymer film with thickened regions in between the wires forming the wire mesh of FIG. 5.

FIG. 12 is a partial cross-section of an alternative embodiment of the encased stent of FIG. 11 showing a layer of endothelial cells on the inner surface of the encased stent.

FIG. 13 is a partial cross-section of a further alternative embodiment of the encased stent of FIG. 11 showing a separate layer on the outer surface of the encased stent for incorporating drugs compatible with the lining of the occluded artery.

FIGS. 16A and 16B are schematics of plasma reactors for use in the practice of the present invention. FIG. 16A is a schematic of a low pressure plasma reactor for surface modification of a stent metal mesh. FIG. 16B is a schematic of an atmospheric pressure plasma reactor for surface modification of the inner wall of a polyurethane encased stent.

FIG. 17 is a schematic of a flow cell for endothelial cell growth studies.

FIGS. 20A and 20B are graphs showing stress/strain curves for polyurethane films at 100% and 200% strain.

FIGS. 26A and 26B are schematic diagrams of a plan view and an elevation view, respectively, of a flat model of a coated stent for tensile testing.

FIGS. 27A-F are optical images of coating on a wire.

FIGS. 28A-L are optical images of a coated wire during tensile testing at 37° C. at strains of 20%, 26.7%, 33.3%, 40%, 46.7%, 50%, 46.7%, 40%, 33.3%, 26.7%, 20%, and 0%, respectively.

FIG. 29 is a stress/strain curve for polyurethane coated stainless steel wire (50% strain).

FIGS. 32A and 32B are phase images of untreated polyurethane surface using AFM scan (1 μm×1 μm) performed at 2 Hz using an etched silicon nitride tip on a tapping mode.

FIGS. 33A and 33B are height images of untreated and plasma treated polyurethane surfaces, respectively, using AFM scans (100 μm×100 μm) performed at 2 Hz using an etched silicon nitride tip on a tapping mode.

FIGS. 35A and 35B are images of immunofluorescense staining of human albumin deposited on stainless steel surface and fibrinogen deposited on metal surface, respectively.

FIGS. 37A-C are fluorescence photomicrographs of aricidine orange stained HCAE cells on plasma treated, collagen treated and fibronectin treated polyurethane coating on glass cover slips, respectively.

FIGS. 38A-C are fluorescence photomicrographs of aricidine orange stained HCAE cells on plasma treated, collagen treated and fibronectin treated polyurethane coating on stainless steel coupons, respectively.

DETAILED DESCRIPTION OF THE INVENTION

Figure 9:
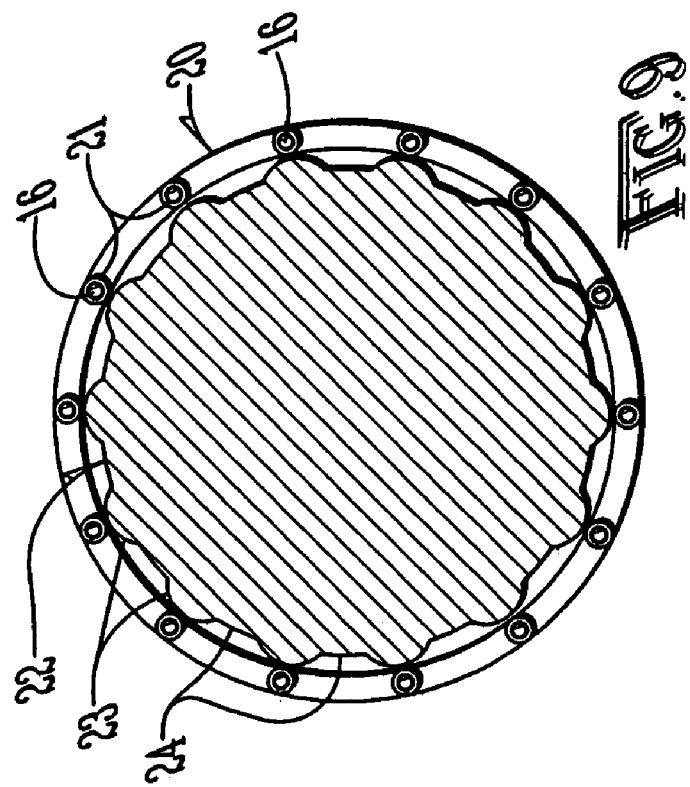
FIG. 9 is a cross-section of the wire mesh of FIG. 5 with the wax core of FIG. 7 inserted therein so that the raised areas of the wax core are placed in proximity to the wires so that when the stent is coated with a polyurethane layer the regions in between the wires are formed with a thicker layer than the areas in close proximity to the wires.

With reference to FIGS. 1-4, the preferred embodiment of the present invention may be described. Angioplastied blood vessels and stented sites frequently re-occlude because of intense coagulation reaction at the lesion site. The current approach to maintain the patency of stent sites focuses on inhibiting platelet aggregation and using agents to prevent smooth muscle cell proliferation. The present invention is a novel stent that utilizes the body's inherent anti-thrombogenic defenses by growing an endothelial cell lining along the inner surface of the stent. A multiple-layer continuous polymer film encases the stent and incorporates anti-coagulant drugs (i.e. heparin), cell cycle inhibitors (i.e. rapamycin), and vascular endothelial growth factors (VEGF), which allow confluent growth of endothelial cell linings to discourage restenosis.

The encased stent employs an endothelial cell lining, the best known defense against thrombosis formation, to prevent restenosis. It also employs a conducting (ligno-pani) biocorrosion-inhibiting coating on the stent wire to prolong the life of the stent against body fluid corrosion.

Unlike the open mesh structures of current stents, the stent of the present invention is encased with a multi-layer polymer film to (1) inhibit bio-corrosion of stent wires, (2) form a continuous film, expandable radially by pressure actuation (stainless steel stents) or by thermal actuation (nitinol stents), and (3) maintain blood flow with minimal wall turbulence. The radially expandable polymer film encasing the stent wires froms a homogeneous thin-walled tube for confluent growth of an endothelial cell lining along the inner surface of the encased stent. The stent may have a corrugated inner wall. The advantage of the corrugated inner wall is that only a small fraction of the inner wall of the stent will be under pressure during expansion, therefore any endothelial cell used for seeding will be preserved for rapid growth of the cell lining.

The polymer film may incorporate (1) anti-thrombin, anti-coagulant and anti-inflammatory drugs for short-term prevention of fibrin attachment and platelet coagulation following stent placement; and (2) VEGF and an extracellular matrix (ECM) structure with embedded gene therapy for rapid growth of an endothelial cell lining on the inner surface of the encased stent to provide protection against restenosis.

The stent encasing process is effective for nitinol shape-memory alloy stents as well as stainless steel stents. Nitinol stents are advantageous in some respects over stainless steel stents, but have not been used extensively because of the possibility of nickel corrosion. The proposed encasement process would provide long-term protection against such corrosion for nitinol stents. The nitinol stents are more adaptable to arterial placement when the lumen diameter is less than 3 mm. Nitinol stents are also expected to be more cost-effective compared to their stainless steel counterparts.

The encased stent of the present invention produces a long-lasting stent that will discourage restenosis by taking advantage of the body's natural arterial defenses against re-blockage. The stents are fully encased by a multi-layer polymer film composed of drugs and cell-growth factors designed to (1) provide a uniform inner surface lined with a protective layer of endothelial cells to prevent platelet aggregation and arterial blockage, (2) prevent inflammatory and toxic reactions to the bare metal stents, and (3) protect the stents' wires against bio-corrosion. In contrast, currently used stents based on open-cell metal wire mesh structures don't permit the formation of an endothelial cell lining.

The use of the encased stent is limited to placement in unbranched arterial segments. If the occluded arterial section has one or more branches, the encased stent can't be used. For branched arteries, the stents can be coated in the same manner but not completely encased, allowing blood to flow through the branched sections. While the coating process is intended to pre-coat the inner wall of the radially expandable stent with endothelial cells, the process requires careful optimization so that, when expanded, the cell monolayer retains its integrity on the tubular surface.

FIGS. 1-4 show the design of the encased stent. A cross-section of a stented artery shows the stent with a continuous polymer film for developing an endothelial cell lining that will prevent platelet deposition or restenosis. The encased stent shown in FIG. 1 may be contrasted with an uncoated wire mesh structure as shown in FIG. 5. Pretreatment of the stent wire with a conducting polymer coating and a hydrophilic polyurethane overcoat provides blood compatibility and a high corrosion resistance. A coupling agent (toluene diisocynate, TDI) is added to the polyurethane coating for attaching hydrophilic polyethylene glycol (PEG), which is grafted onto the inner surface as shown in FIGS. 10-13. The Polyurethane-TDI—PEG structure acts as a host to different drugs and AT3 for stopping thrombus formation. The TDI coupling agent attaches polyethylene glycol (PEG) molecular chains in such a way that one end of the long PEG molecules is attached to the polyurethane and the other end remains free to provide steric hindrance against deposition of platelets. The PEG molecules entrap drug particles and form covalent bonds with other chemicals such as heparin to provide the desired blood compatibility.

Figure 8:
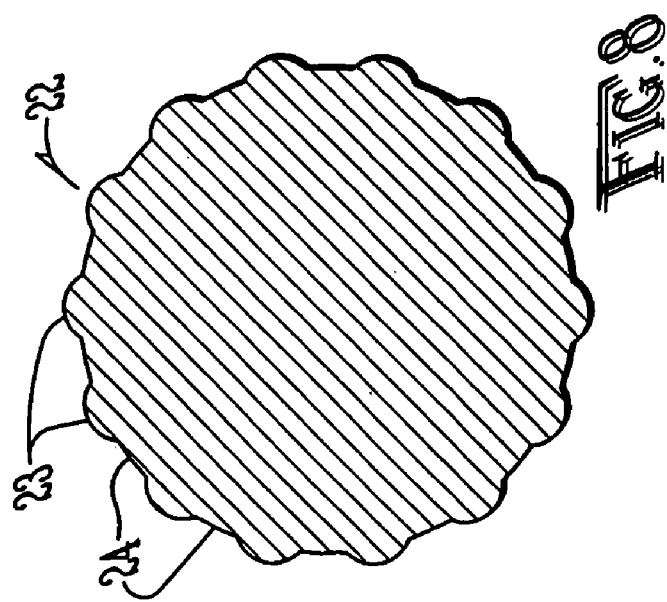
FIG. 8 is cross-section of the wax core of FIG. 7 showing raised areas of the polymer film corresponding to the location of the wires of the wire mesh of FIG. 5.

FIGS. 5-9 show the stent coating process. First, the metal stent wires are coated with a biocorrosion inhibiting conducting polymer (ligno-pani) as a primer to provide protection against corrosion by body fluids. The second step of the coating process is the encasement of stent wires with a radially flexible thin polymer film made from polyurethane and polyethylene glycol (PU—PEG). The open mesh structure of the metal stent is covered with the thin polymer film to promote the growth of a confluent endothelial cell lining on the inner wall of the encased stent. In order to form a continuous film over the open mesh wire structure a wax core with a grooved surface is used to apply the continuous polymer film as shown in FIGS. 7-9. The diameter of the wax core is such that the stent fits closely over the grooved core as a sleeve. A thin film of medical-grade polyurethane is applied to the conducting polymer coated stent. The film thickness varies according to shape of the wax core to achieve the optimum thickness that allows flexibility and uniformity during radial expansion of the encased stent. Once expanded, the inner surface of the encased stent must be substantially uniform to support the confluent growth of an endothelial cell lining after the stent is placed in the artery. In the preferred embodiment, only the coatings on the inner surface of the stent contains anti-coagulant drugs, cell cycle inhibitors, and vascular endothelial cell growth factors. As shown in FIG. 13, however, other drugs may be employed on the outer surface of the stent for particular applications. Candidate drugs and cell growth factors are shown in Table 1.

TABLE 1

Candidate drugs to incorporate in stent coating.

| Candidate Drugs | Action |
| --- | --- |
| Heparin/Aspirin | Anti-Coagulant/Anti-Inflammatory |
| Rapamycin | Immunosuppressant & Anti-Inflammatory |
| Cipro-floxacin | Antibacterial (Infection Resistance) |
| Paclitaxel | Prevents Cell Proliferation |
| Diazeniumdiolate | Nitric Oxide (NO) Emission |
| iNOS and Ca2+ influx | Endothelial Stimulation for NO Emission (induced Nitric Oxide Synthase) |
| Gene Suppression | Reduces Cell Proliferation: Suppression of c-myc Gene Expression |
| ReoPro | Clot-Blocking Drug |

As shown in FIGS. 1 and 2, the encased stent 10 is employed by inserting it into an artery 11 having an occluded section 12 using an angioplasty balloon 13. FIG. 2 shows the stent 10 as it would appear in cross-section in the occluded artery 11 with the angioplasty balloon 13 in position within the stent 10 and before expansion of the balloon 13; Note that the continous polymer film 14 of the stent 10 comprises thick regions 15 between the stent wires 16 and thin regions 17 in proximity to the stent wires 16.

As shown in FIGS. 3 and 4, the stent 10 is expanded against the inner walls of the occluded artery 11 as the angioplasty balloon 13 is expanded. The thick regions 15 thin as the stent 10 is expanded and the stent wires 16 move farther apart. After the angioplasty balloon 13 is removed, the polymer film 14 is substantially smooth and provides a suitable surface for the growth of an endothelial cell lining on its inner surface 18.

The process of manufacturing the encased stent 10 of the present invention may be described with reference to FIGS. 5-9. A wire mesh tube 20 comprising individual stent wires 16 of stainless steel or nitinol provides the foundation of the encased stent 10. A wire mesh tube of this type of typical of conventional stents. The wires 16 forming the wire mesh tube 20 are first coated with a corrosion inhibiting layer 21, using a material such as ligno-pani.

Figure 10:
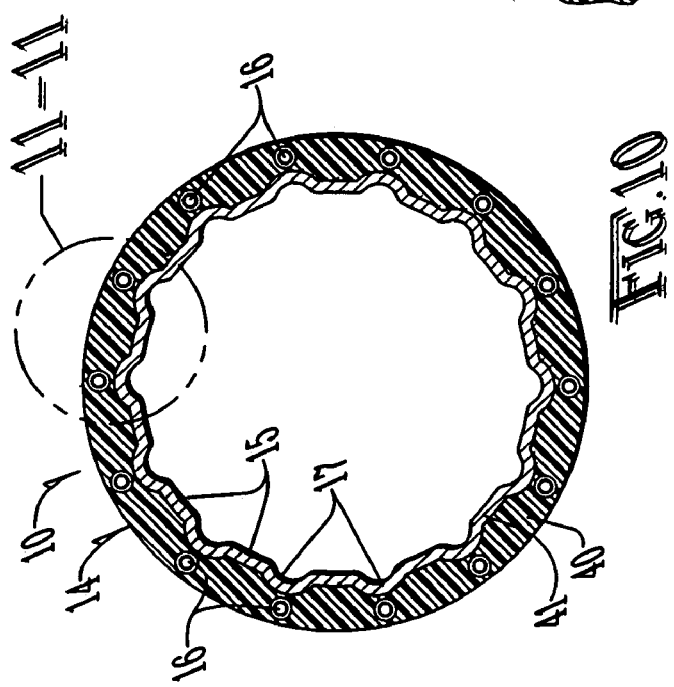
FIG. 10 is a cross-section of an encased stent having a continuous polymer film coated thereon.

Next, a knurled wax core 22 is prepared for forming an encased stent 10. The wax core 22 is formed with raised areas 23 and depressed areas 24 for forming a continuous polymer film 30 as shown in FIG. 10 having thick regions 15 in between the wires 16 forming the wire mesh tube 20 and thin regions 17 in proximity to the wires 16.

As shown in FIG. 9 the wax core 22 is inserted in the wire mesh tube 20 so that the raised areas 23 of the wax core 22 are placed in proximity to the wires 16. When the wire mesh tube 20 is coated with polyurethane, a continuous polyurethane film 40 having thick regions 15 formed in between the wires 16 and thin regions 17 formed in close proximity to the wires 16 is created as shown in the cross section of FIG. 10.

Figure 11:
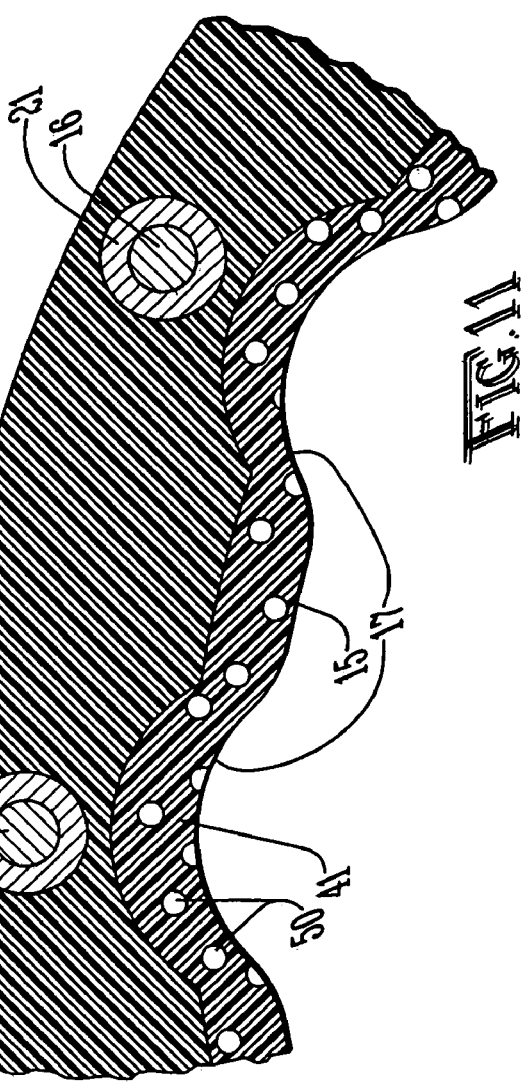
FIG. 11 is a partial cross-section of the encased stent of FIG. 10 expanded in the area of the circle 11-11 of FIG. 10. The expanded partial cross-section reveals the corrosion inhibiting layer coated on the wires and the continuous polymer layer film having varying thicknesses to allow for uniform expansion of the stent into a substantially smooth surface. The polymer film comprises a polyurethane layer and a polyethylene glycol layer incorporating various drugs and cell factors on the inner surface of the encased stent. The polyurethane layer and the polyethylene glycol layer are coupled by a toluene diisocyanate coupling agent which is not shown.

Once the polyurethane layer 40 is formed, the next part of the polymer film 14 is coated thereon. As shown in FIGS. 11-13, the polymer film 14 comprises a corrosion inhibiting layer 21 coated on the wires 16, a continuous polyurethane film 40 having varying thicknesses to allow for uniform expansion of the stent into a substantially smooth surface, and various layers incorporating drugs and cell factors 50. In the preferred embodiment, the polymer film 14 comprises a polyurethane layer 40 and a polyethylene glycol layer 41 incorporating various drugs and cell factors 50 on the inner surface 51 of the encased stent 10. The polyurethane layer 40 and the polyethylene glycol layer 41 are coupled by a toluene diisocyanate coupling agent which is not shown.

An alternative embodiment of the encased stent 10 is shown in FIG. 12 wherein a layer of endothelial cells 55 is formed on the inner surface of the polyethylene glycol layer 41 prior to placement of the encased stent 10.

FIG. 13 shows a further alternative embodiment of the encased stent 10 having a separate polyethylene glycol layer 53 on the outer surface 52 of the encased stent 10 for incorporating drugs 54 compatible with the lining of the occluded artery.

EXAMPLES

Coating Process for Nitinol

There are three requirements for the successful coating of stents:
1) Uniformity of coating to prevent corrosion of metals for a long period, often in excess of twenty years.
2) Flexibility of coating to remain as an effective film over the NiTi wires during multiple contractions and expansions, not only during the placement of stents but also throughout the lifetime of the stents as the artery narrows and widens from the blood flow. This arterial degeneration is due to the pulsation of the artery from the blood flow continuously rubbing against the stent.
3) Biocompatibility of the coating; while protecting the NiTi stent from corrosion, the coating material must not cause any cell damage, bacterial adherence, and adverse tissue reaction, undue allergic or foreign body reactions, and, most importantly, the coating should be effective in reducing the probability of restenosis.

While there are a number of methods available to coat a metal surface, the coating of stents presents a difficult problem. Stents are made of thin wires (the wire diameter is approximately 100 µm) forming a lattice tube. The stent diameter is often very small (about 4 mm), making it difficult to coat both the inner and outer surface uniformly with a thin film. In general, a thin film coating with a film thickness less than 50 µm will provide a good adhesion of the film to the metal surface and better flexibility or mechanical properties compared to a thick coating.

In most cases, a metal surface is coated by spraying a polymer paint on the surface using a spray nozzle. The paint is first dissolved in an organic solvent before spraying. After the liquid paint coats the surface, the organic solvent evaporates, leaving the polymer film. Such a liquid spray coating may not be very effective in coating a tube of wire mesh with a uniform coating on both the inner and outer sides of the wire mesh. An electrostatic powder coating may provide a more uniform coating on the stent strut (wire mesh) surface than the liquid based spray coating could provide. The specific size of the powder particles allow for a control of thickness, but powder coating is not ideally suited for three-dimensional structures such as stents. Another form of liquid coating is known as dip coating, which involves dipping the substance within the liquid paint. This also provides a uniform coating, but it compromises the control over precise coating thickness. Commercially available biomedical grade polyurethane can be used (Tecoflex, Thermeties, Woburn, Mass.) for spray or dip coating.

There are two purposes for coating NiTi stents: 1) to minimize the corrosion of Ni and 2) to incorporate drugs that make the stent biocompatible, acting as an anticoagulant agent. The surface of a nickel-titanium alloy develops a layer of titanium oxide ($TiO_2$). The oxide layer appears as a dark film over the metal. The oxide layer can serve as a natural coating for corrosion resistance. The oxide layer, however, cannot prevent nickel leaching out of the NiTi substrate into the body.

The three types of polyurethane coating methods used (dip coating, aerosol spray coating, and brush coating) all produced good coverage but the film thickness varied. The differences in the thickness of the coating encountered within a given area required measurements to be recorded for the mean value of the film thickness. The aerosol spray coating method, though it produced a nonuniform coating surface, was the most effective at providing control over the coating thickness. Using a set distance of 0.1 meters and varying the spray exposure time allowed specific increments of the average thickness of the polyurethane coating.

The coating process for Nitinol coupons (NiTi alloy, Shape Memory Alloys, Inc.) involved liquid based polymer coatings and antithrombogenic drugs. The surfaces of twelve coupons were first polished with relatively coarse Emory 300 sandpaper, followed by a much finer grain Emory 600 sandpaper to remove the oxide layers. Each coupon was approximately 2.5 cm×2.5 cm with a thickness of 0.1 mm. Five coupons were brush coated with polyurethane for varying film thicknesses. The film thickness was measured with a permascope (Fischer Instruments Model No. D211D). The mean thickness and standard deviation were noted for each coating. Another five coupons were coated with polyurethane and aspirin particles, serving as an effective anticoagulant and anti-inflammatory drug. Aspirin particles were applied by two techniques, as described below, using a powder coating process. Two coupons were coated with polyurethane and nebulized aspirin aerosol. The coupons were placed horizontally for the coating to become uniform. After 30 minutes, each coupon was placed in a curing oven for 10 minutes at 100° C. to facilitate drying.

The variation of film thickness applied by brush coating on two Nitinol coupons are shown in Tables 2 and 3. For a flat coupon or substrate, the brush coating provided a good control of film thickness in the range of 20 to 60 µm. For a finer film thickness, dip and spin coating methods can be used. Literature studies on liquid paint coatings show that two to three layers of film coatings applied to a substrate provide a stronger film adhesion compared to a single film coating.

TABLE 2

Variation of thickness of polyurethane film on Nitinol coupons.

| | Film Thickness (μm) | |
|---|---|---|
| Measurement | Coupon 1 | Coupon 2 |
| 1 | 30.48 | 22.10 |
| 2 | 29.46 | 21.34 |
| 3 | 27.43 | 22.10 |
| 4 | 29.21 | 22.10 |
| 5 | 28.96 | 22.10 |
| 6 | 30.48 | 22.10 |
| 7 | 31.24 | 19.30 |
| 8 | 29.97 | 21.59 |
| 9 | 28.45 | 21.84 |
| 10 | 30.23 | 22.10 |
| 11 | 29.97 | 21.34 |
| 12 | 28.70 | 21.84 |
| 13 | 28.96 | 22.35 |
| 14 | 29.46 | 21.34 |
| 15 | 29.21 | 21.08 |

TABLE 3

Statistics of film thickness variation.

| Statistical Analysis | Coupon 1 | Coupon 2 |
|---|---|---|
| Average Thickness | 29.46 μm | 21.84 μm |
| Standard Deviation | 0.76 μm | 0.51 μm |
| Relative Standard Deviation | 4% | 3% |

Coating Process for Glass and Plastic Slides for Cell Growth Studies

Transparent substrates were used for direct microscopic examination of cell adhesion on coatings with and without drugs. Standard glass microscope slides and clear plastic substrates (2.5 cm×2.5 cm) were coated with polyurethane (PPG) and polyurethane grafted with aspirin for biocompatibility studies. Three polyurethane coated plastic slides, three aspirin coated plastic slides, two polyurethane coated glass slides, and one aspirin coated glass slide were prepared. Each slide was brush coated with polyurethane to obtain a film of approximately 50 μm in thickness. The slides were placed horizontally within a curing oven for another thirty minutes at 50° C. to facilitate drying. Three bare plastic slides and one bare glass slide were allotted for cell growth studies.

The brush coating procedure provided a relatively uniform, air bubble-free coating on only one side of the substrate. The slides were coated with aspirin particles while the film was still wet, facilitating the encapsulation of aspirin into the coating. The first technique for aspirin incorporation was grinding aspirin with a mortar and pestle, and then sieving the powder with a 40 μm×40 μm fine sieve opening. The drug particles develop a wide size distribution ranging from a few micrometers to 40 μm in diameter over the wet polyurethane film. The first layer of aspirin was completely absorbed and sank to the bottom of the paint. The repeat coatings at fifteen-minute intervals created several layers of aspirin within the coating, along with surface-exposed aspirin. Therefore, the multilayer aspirin coating has a time-release drug property, as aspirin is slowly released by dissolution through the coating. The other technique used was the nebulized solution of aspirin. The aerosolization of aspirin provided a much more uniform distribution of fine particles (1-5 μm in diameter) for the aspirin. The nebulized droplets must be dried to form solid aspirin particles before coating. Multiple coatings of nebulized aspirin were applied for an even release of medicine. For plastic coupons, a brush coating method was used, and aspirin was deposited with both dispersion and nebulizer techniques.

Corrosion Tests

Corrosion is an electrochemical reaction in which metal ions are converted to metal ions resulting in its continuous degradation to oxides, hydroxides, and other compounds. Human body fluid contains water, various ions such as chlorides, hydroxide, metal ions dissolved in oxygen, and proteins. The body fluid is therefore corrosive to metals and alloys. Stainless steel and Nitinol are both alloys and undergo corrosion. The corrosion rate is the rate at which metal atoms are converted to metal ions per unit of time. The corrosion current in a synthetic physiological solution can be measured by using a Potentiostat/Galvanostat Corrosion Analyzer. The corrosion rate of a NiTi alloy can be measured with a potentiostat. The stent material can be exposed to the synthetic body fluid within an electrochemical cell. The cell contains a reference, counter, and test electrode within the solution, and the corrosion current is measured between the electrodes. Either a NiTi coupon or a NiTi stent can be exposed to the solution depending on the type of cell used. An immersion cell exposes the entire stent to the solution, while a flat cell exposes 1 $cm^2$ of the NiTi coupon to the solution. The physiological solution is commercially available as Ringer's Solution or Hank's Salt Solution.

The corrosion current is measured in nanoamperes/$cm^2$ from which the dissolution or corrosion rate of metal is determined in terms of mm/yr. The lifetime of stents depends upon thickness of the wires that intertwine to make up the stent. For example, if the wire diameter is 100 μm, and the corrosion rate is 20 μm/year, the service lifetime will be less than five years, since corrosion reduces the mechanical strength; the wire diameter can be reduced to a level where the stent supporting the artery structure will not have enough strength to maintain supporting the artery.

Metallic corrosion takes place in two electrochemical reactions. One is called an anodic reaction, or oxidation, and the other is called a cathodic reaction, or reduction. Both cathodic and anodic reactions take place on the surface of metal. There are large numbers of cathodes and anodes that are formed close to each other on a metal surface undergoing corrosion. Both of these reactions, called half reactions, occur on the metal surface, contributing to corrosion. Therefore, there are two components of a corrosion current; one is the anodic branch and the other is the cathodic branch, with respect to a zero current reference point (inflection point; i=0), as shown in a Tafel plot. These currents can be measured by applying a potentiostat or voltage on the metal surface with respect to a reference electrode when the metal surface and reference electrode are immersed in an electrolyte, a solution of salts in water. In the test measurements, Ringer's Solution can be used to determine the corrosion rate in the body fluid. A specifically designed software application (SoftCORR Corrosion Analysis Software) is used to calculate the corrosion rate from Tafel plots.

Coupons (2.5 cm×2.5 cm×0.01 cm) made of stent material (Nitinol) were tested for corrosion rates both with and without a coating. Two types of coatings were used: 1) polyurethane coatings with a coating thickness varying from 3 to 50 μm, and 2) polyurethane coating with antithrombogenic drug particles (in this research, aspirin was used). Tafel plots for each case were analyzed to determine the corrosion rate.

Corrosion Reaction:

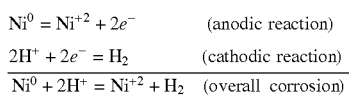

The anodic and cathodic corrosion currents and corrosion rates were measured using a potentiostat instrument. In all experiments with corrosion cells, the test coupons were exposed to an electrolyte solution for at least 24 hours before corrosion measurements were taken. This extended exposure stabilizes the electrochemical reactions. Initially, the corrosion current varies greatly until the substrate undergoes significant passivation. The variation of current with respect to time decreases substantially within a period of two hours.

For corrosion studies using the potentiostat's electrochemical cell, Ringer's Solution was used to simulate the exposure of the nickel-titanium coupons to body fluid. The corrosion rate, as a function of film thickness, shows fluctuations due to varying corrosion sites. The regression analysis was performed. The rate of NiTi corrosion in Ringer's Solution decreased from 29 μm/year to approximately 13 μm/year when the coating thickness was increased to 30 μm. Fluctuations were reflected in the deterioration of the Tafel plot curves, reducing the accuracy of the corrosion rate equation fits.

Figure 14:
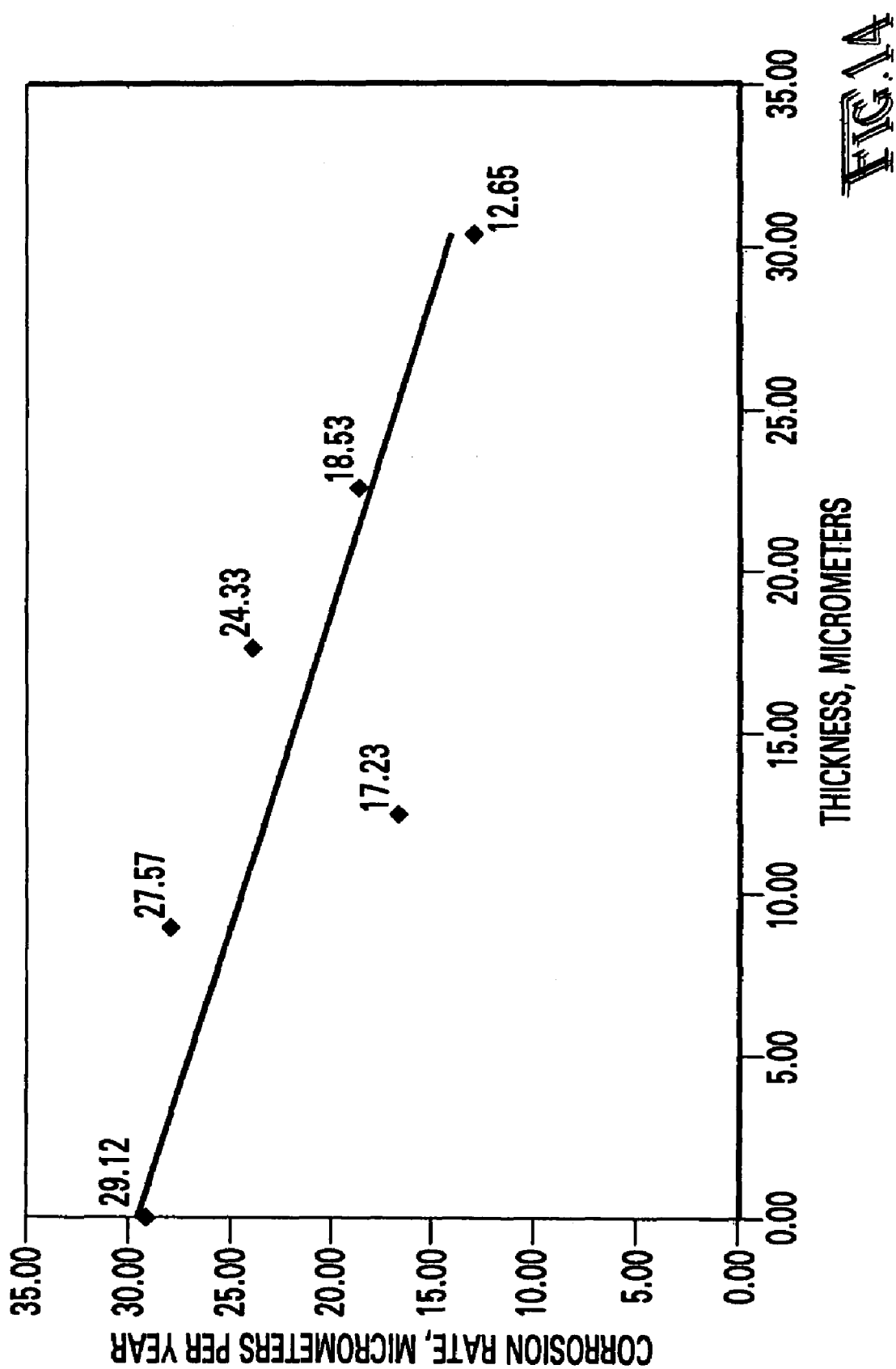
FIG. 14 is a graph of corrosion rate versus thickness of a polyurethane anticorrosion coating.

Corrosion tests were performed with a Potentiostat (Princeton Applied Research EG&G Potentiostat/Galvanostat Model 283 Corrosion Test Analyzer with a Model 5210 lock-in amplifier) to determine the effectiveness of a polyurethane coating for corrosion prevention over an extended period of time as shown in FIG. 14. Potentiodynamic cyclic corrosion tests were carried out using the test cell referred to in ASTM G5-82 Standard Practice and the electrode assembly specimens reported in ASTM G61-78 Standard Practice. Coated and uncoated coupons were individually exposed to Ringer's Solution (Artificial Physiological Solution containing Sodium Chloride 0.684%, Potassium Chloride 0.035%, Calcium Chloride (Dihydrate) 0.037%, Magnesium Chloride 0.120%, and Sodium Bicarbonate 0.208% (Carolina Science and Math Supply) in the electrochemical cell. The potentiostat open circuit potential stabilized within thirty minutes, after which corrosion tests were performed.

In order to test the linearity of the corrosion rate as a function of the film thickness, Student's t tests were performed as shown in Table 4. First, considering the film thickness as the variable x and the corrosion rate as y, the correlation coefficient (r) was calculated. The value of r was found to be −0.85. The calculated value of $S_r$ is 0.263. Therefore, the value of t is 3.23. From the table of critical values of Student's t distribution, if n−2=4, the minimum value of t is 2.776 for a 95% probability that the relationship between the two variables is linear. Therefore, the experimental data shows that the corrosion rate is inversely proportional to the film thickness of the coating. The objective was to determine the required coating thickness for reducing the stent wire corrosion rate over a period of at least five years after implantation. Since the wires are approximately 100 μm in diameter, a corrosion rate under 10 μm/yr should keep the stent structurally strong.

From the table of critical values of student t distribution, if n−2=4, the minimum value of student t is 2.776 for 95% probability that the relationship is linear. Therefore, the data clearly show that the relationship between corrosion rate and coating film thickness is linear and has a negative slope.

TABLE 4

Corrosion rate ($y_i$ in μm/yr) vs film thickness ($x_i$ in μm).

| Coating Film Thickness in μm = (x) | | | Corrosion rate in μm/year = (y) | | | |
|---|---|---|---|---|---|---|
| $x_i$ | $x_i - x$ | $(x_i - x)^2$ | $y_i$ | $y_i - y$ | $(y_i - y)^2$ | $(x_i - x)(y_i - y)$ |
| 0.00 | −15.45 | 238.7 | 29.12 | +7.54 | 56.85 | −116.49 |
| 8.89 | −6.56 | 43.03 | 27.57 | +5.99 | 35.88 | −39.29 |
| 12.70 | −2.75 | 7.56 | 17.23 | −4.35 | 18.92 | +11.96 |
| 17.78 | +2.33 | 5.43 | 24.33 | +2.75 | +7.56 | +17.61 |
| 22.86 | +7.41 | 5.49 | 18.53 | −3.05 | 9.30 | −22.60 |
| 30.48 | +15.03 | 225.90 | 12.65 | −8.93 | 79.74 | −134.18 |
| | | 526.11 | | | 208.26 | −282.99 |
| | x = 15.45 | | | y = 21.58 | | $S_{xy}$ |

Figure 15A:
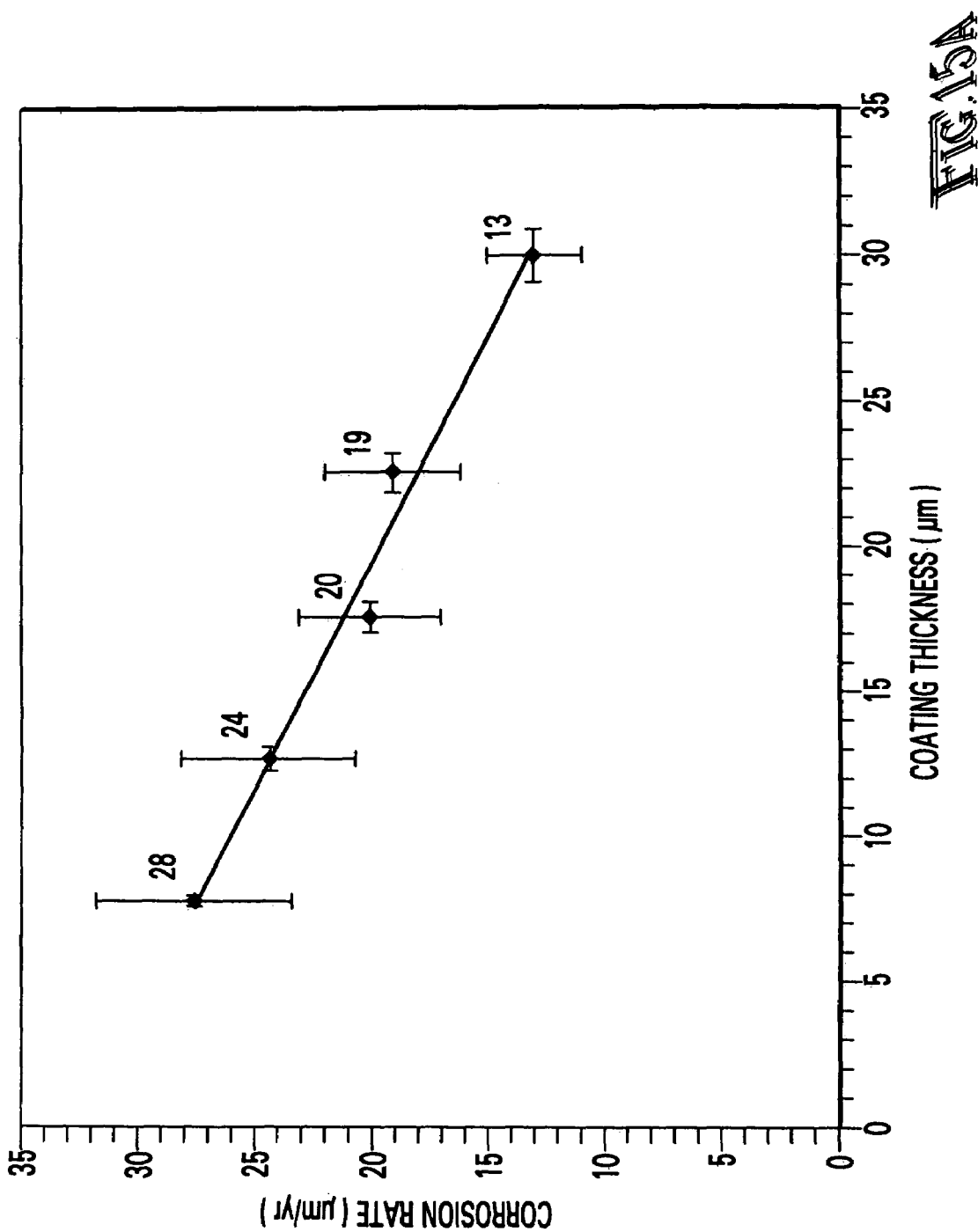
FIGS. 15A and 15B are graphs of further tests of corrosion rate versus thickness of a polyurethane anticorrosion coating.
Figure 15B:
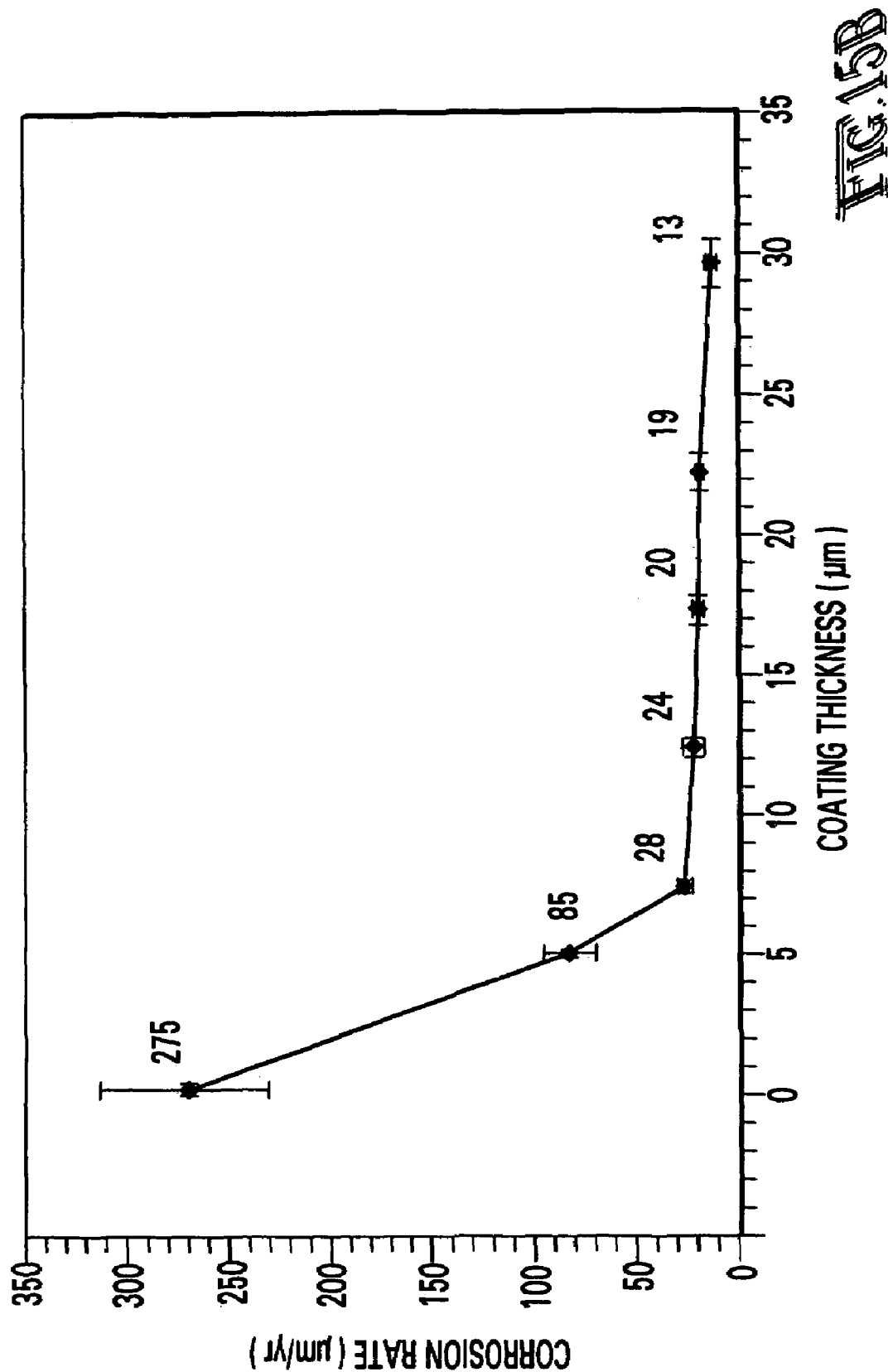

FIGS. 15A and 15B show graphs of a further series of tests of corrosion rate versus thickness of a polyurethane anticorrosion coating.

Biocompatibility & Cell Adhesion

Biocompatibility refers to the interaction between the medical device being tested, the tissues, and the physiological systems involved. The testing depends upon several factors, including the material used, the types of tissue exposed to the materials, and the duration of exposure. A basic guideline for biocompatibility testing is given by the ISO/ANSI/AAMI Standard 10993, Biological Evaluation of Medical Devices. In general, biocompatibility testing requires chemical analysis, in vitro tests, and animal model studies.

Since a stent comes in contact with plaque, endothelial cells, and blood, the biochemical interaction and cellular responses, including blood compatibility tests, must be performed to assess biocompatibility. The thrombogenicity assay can be performed in vitro by having an experiment where fresh blood is allowed to flow through the stents for coagulation studies.

Materials used for stents and coatings can cause foreign-body reactions. For example, nickel in Nitinol stents can cause cellular inflammation, allergic reactions, and even cancer. It is extremely toxic in high concentration levels within the body. Preventing nickel from leaching out of NiTi alloys is a necessary step to improving the biocompatibility of stents. Generally, stents are electropolished to provide a smooth, corrosion-resistant surface. However, pitting corrosion has been observed on the surface of the stents, so a more effective method of corrosion prevention is needed, such as polymer coating. However, the polymer must also be biocompatible within the body. Polyurethane is used for many biological implants.

For biocompatibility assessment, cells were grown on coated and uncoated slides within seven petri dishes. The number of cells that grew on the surface of each slide was an indicator of biocompatibility and cell adhesion viability. The measurements were based on the number of cells as a function of surface area. The media consisted of 13 ml DMEM containing 10% fetal bovine serum and an antibiotic agent, Penicillin Streptomycin. Ten milliliters of COS-7 cells (ATCC immortalized COS-7 monkey kidney cells) in suspension were added by pipette. The petri dishes were placed in an incubator at 37° C. with 5.0% $CO_2$. After 72 hours, the substrates were moved into new dishes. The nitinol coupon was placed into a separate petri dish. The cells were trypsinized with a 1×dilution of trypsin/0.03% EDTA solution.

A hemacytometer (C. A. Hausser & Son Max Levy: Fuchs Rosenthal Ultra Plane Scientific Hemacytometer) and a microscope were used for cell counting. A coverslip was placed over the hemacytometer and 20 µL of the cell suspension was drawn under the coverslip via capillary action. The number of cells within a volume of 1 mm×1 mm×0.2 mm was counted. The cell concentration in the suspension was obtained by multiplying the cell count by a factor of $5.0 \times 10^3$. The total number of cells in the petri dish containing 5 ml of media was obtained by multiplying the cell concentration by five.

Cell growth studies were carried out on bare substrates, substrates coated with only polyurethane, and substrates coated with aspirin powder embedded in the polymer film. When nitinol coupons were used as a substrate for cell growth studies, it was found that the inverted microscope used for cell studies could not be used for the opaque substrate. Transparent slides were used to examine cell growth.

In order to test if the type of substrate relates to a difference in cell concentration on the overlaying polymer film, both glass and Nitinol substrates were coated with a polyurethane film and the cell concentrations per unit area were measured. The results show that the effectiveness of film coatings can be studied on transparent substrates as well as opaque metals.

When cell growth studies were conducted with aspirin-containing polyurethane slides, the COS 7 cells were unable to normally adhere to the coating surface, but an extremely small number of cells were found to have adhered to the surface. It may be construed that the release of aspirin prevents the cells that attempt to attach to the surface from surviving. Therefore, aspirin would be effective at preventing thrombogenesis around the nickel titanium stent. However, the concentration of aspirin must be low enough to prevent damage to normal endothelial cells within the artery. The results show that the addition of an antithrombogenic drug may interfere with endothelial cell growth. Therefore, addition of endothelial cell growth factors with drug addition must be adjusted accordingly.

Stress/Strain Behavior of Polyurethane Coatings

A biocompatible polyurethane, ChronoFlex® AR (CT Biomaterials, Woburn, Mass.) may be used in the present invention. This material is a medical-grade polyurethane that has passed or exceeded all requirements specified in the USP Class VI biocompatibility tests. ChronoFlex® AR elastomers are polycarbonate based, and are believed to be resistant to environmental stress cracking during the intended period of implantation.

Polyurethanes typically have a high tensile strength (7500 psi) and elongation to break (500%). As shown below, a coating on a stent will have to expand up to 225% upon expansion of the stent in the artery. However, although polyurethane has a large elongation, the elastic limit is less than approximately 50%. It is important that the polyurethane coating does not exceed its elastic limit, otherwise plastic deformation and cracking in the coating may occur over prolonged strain, especially in the corrosive environment of the body.

Previously, coatings of stents have been applied to the metal framework of the stent itself, whether for a balloon-expandable stent (BX), typically made from 316L stainless steel, or a self-expandable stent (SX) made from shape memory alloy (SMA) such as nitinol. The present invention encapsulates the metal framework in a polyurethane tube.

The stent may be considered a tube that is expanded by air pressure. Pressures applied to any cylindrical structure result in a hoop, or circumferential-loading of the vessel. The applied pressure and the hoop stress have the same units but differ in direction. While hoop stress, total hoop force and pressure are equivalent descriptors of the vessel forces, the hoop force is the more relevant as it correlates to the strength or maximum hoop load that can be carried by the coating without failure. Failure would occur when the hoop stress exceeds the ultimate tensile strength (UTS) of the polymer coating.

The elastic response of a device to an applied load is known as the stiffness. The stiffness of the stent is an important quantity as it describes the effectiveness of the stent in resisting diameter loss once expanded due to the blood vessel "recoil." Stiffness is the inverse of compliance, the diameter change at a specific applied pressure. The radial compliance of a stented vessel is important in the design of a stent such that the native physiological vessel proportions are maintained as close as possible.

SX stents are typically manufactured at the vessel diameter or slightly greater and then crimped until used. Upon delivery to the vessel, the constraint is removed. A balloon is still deployed, but the self-expansion of the SMA assists the balloon expansion compared to that of a stainless steel BX stent which resists the balloon expansion. For example, a stent having an actual diameter of about 10.5 mm may be crimped to 4 mm and then expanded where it recoils to 8.5-9 mm. Any coating on this stent would therefore undergo an expansion of up to 225%.

Figure 19:
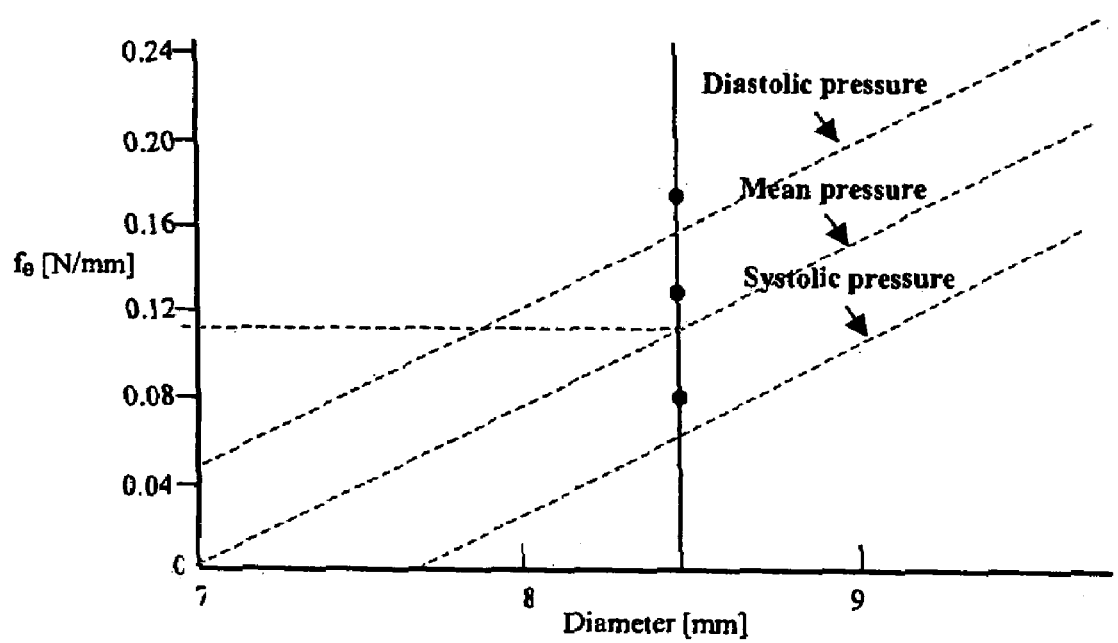
FIG. 19 is a graph showing the dynamic effects of a deployed stent.
Figure 18:
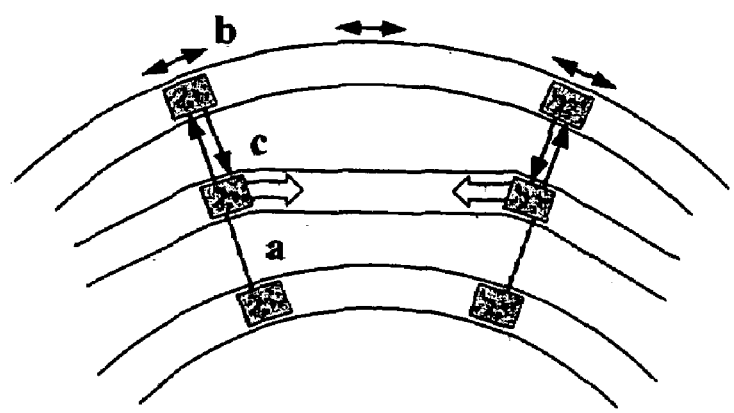
FIG. 18 is a schematic diagram illustrating the expansion of a balloon expandable stent.

A cross-section of an expanding BX stent is shown in FIG. 18. Here the coating and stent struts are expanded by the balloon from a to b. Upon deflation of the balloon, the hoop stress and the arterial wall stress compress the stent and coating back to c. With the balloon now not supporting the coating film, it will be likely to minimize strain by flattening out as shown with residual stresses acting in tension upon the stent famework. Dynamic effects after deployment are illustrated in FIG. 19, where the diastolic and systolic pressures are shown.

Stress/strain experiments were performed on films of different thicknesses of a biocompatible polyurethane (ChronoFlex® AR, CT Biomaterials). Thin films were prepared on PTFE flat sheets and tensile (stress/strain) tests were performed at 100% and 200% strain in an Instron equipped with an environmental chamber. The films were tested at 37° C. to simulate body temperature. The results for two films with thicknesses of 290 µm and 230 µm, respectively, as measured on a Permascope, as shown in FIGS. 20A and 20B.

For both films, the plots were similar, except that the stress required to produce the same strain was slightly higher for the thicker film. For the 200% strain film, the force per unit length required was observed to be ~0.95 N/mm, which is far higher than the maximum equilibrium force for an SX stent of ~0.22 N/mm, as described for a 10.5 mm SX stent by Deurig et al., "An overview of superelastic stent design," Min. Invas Ther. & Allied Technol., 9(¾), pp. 235-246, 2000. However, extrapolating results of tests on films of thicknesses ranging from 150-500 µm showed that a film of ~30-50 µm would suffice and not result in chronic acute recoil.

A further observation from the stress/strain curves is that a residual strain of 8-30% remained in the films after unloading. This may be attributed to the disruption of the hard segments in the polymer. The chemistry of the hard and soft segments and the degree of phase separation can significantly affect the stress/strain behavior. Hard segment crystallization has been found to increase this hysteresis.

Surface Tension

As pointed out above, the polyurethane films will be strained when in actual use up to 225%. In general, there are three macroscopic properties of a surface of a solid containing more than one chemical element; the surface tension, the surface stress, and the specific surface free energy. The surface tension, $\gamma$, is defined as the reversible work done in creating a unit area of new surface at constant temperature, volume and total number of molecules. For a solid undergoing an isotropic strain, it will not deform isotropically as some directions on the surface will deform more easily than others, therefore the surface tension will vary with strain. The surface roughness will also change under strain due to the flattening out of the peaks and valleys and it is well known that surface roughness is also a factor on the surface tension.

The critical surface tension ($\gamma_{crit}$) as defined by Zisman ("Relation of the equilibrium contact angle to liquid and solid constitution," in *Contact Angle. Wettability and Adhesion*, R. F. Gould (Ed.), ACS, Washington, D.C., 1964) is that in which the liquid has a surface tension equal to, or less than, the value required to completely wet and spread spontaneously on the surface. Baier ("The role of surface energy in thrombogenesis," Bull. NY Acad. Med., 48, pp. 257-272, 1972) established a correlation between the critical surface tension and thrombogenecity in which there is a region of minimum $\gamma_{crit}$ where biological interaction between the body and the biomaterial is at a minimum. Recent work by Selvaduray and Bueno ("The critical surface tension of 316L stainless steel: Implications for stent thrombogenicity," Paper presented at ASM Matls. & Proc. for Med. Dev. Conf., Anaheim, Calif., 8-10 Sept. 2003) showed that electropolished stainless steel stents were within Baier's zone of biocompatibility even when strained up to 15%.

Figure 21A:
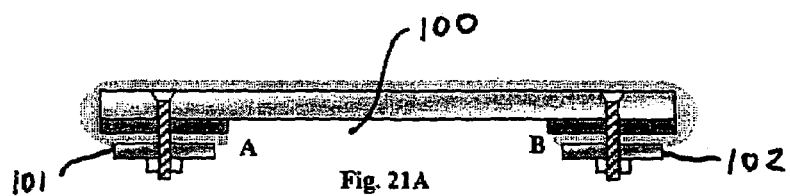
FIGS. 21A-C are an elevation, bottom plan and top plan views, respectively, of a device for holding strained polyurethane film for surface tension testing.
Figure 21B:
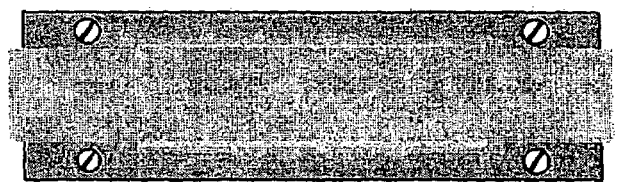
Figure 21C:
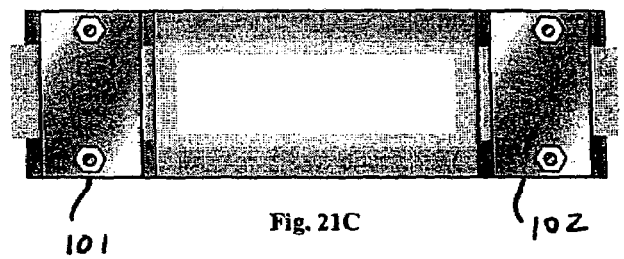
Figure 22:
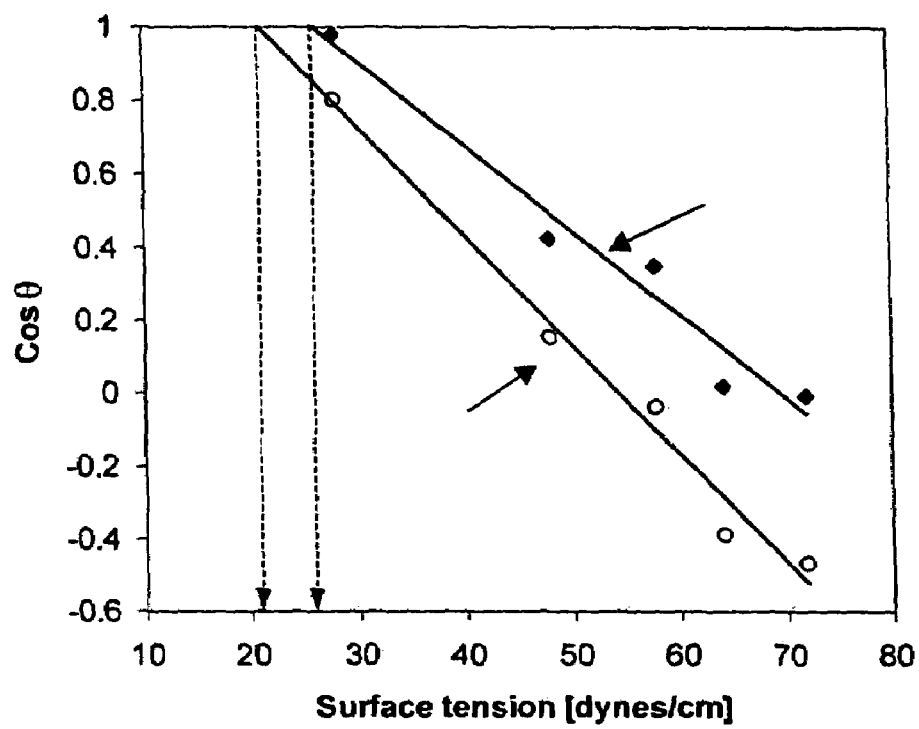
FIG. 22 is a Zisman plot for PTFE and polyurethane.
Figure 23:
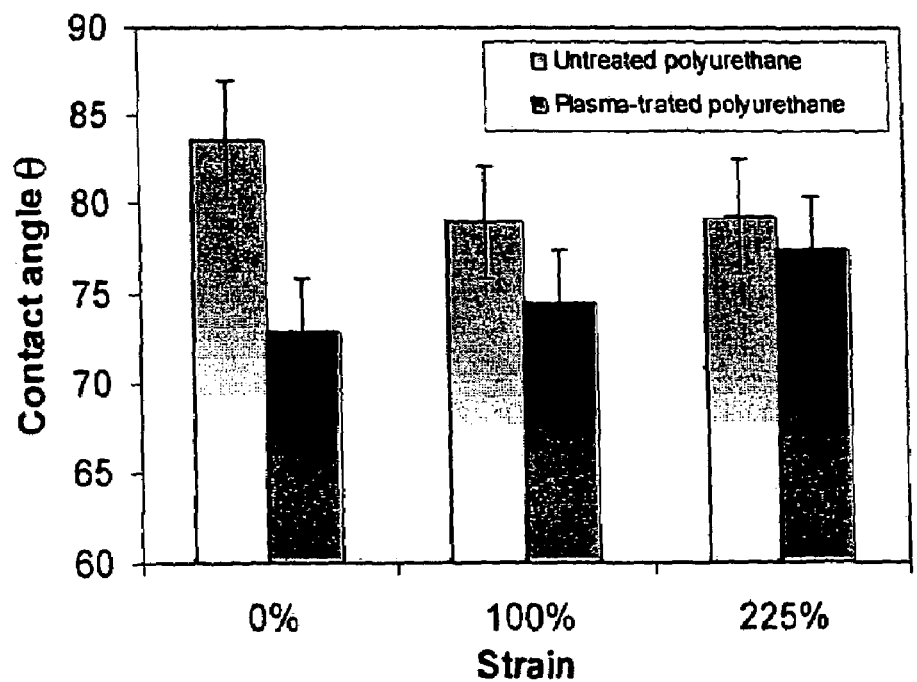
FIG. 23 is a graph showing the variation in contact angle for water for strained polyurethane film before and after plasma treatment.

A small platform was designed in which a length of polyurethane film can be strained to different amounts and clamped, as shown in FIGS. 21A and 21B. The device is designed where the gap 100 between the clamps 101, 102 fits over the specimen stage of the VCA Optima so that several points on the film may be measured. A Zisman plot for PTFE (control) and polyurethane is shown in FIG. 22. The liquids used were water, glycerol, formamid, ethylene glycol and benzene. From this plot it is observed that the critical surface tension for cast untreated polyurethane is ~26 dynes/cm. The contact angle for polyurethane films stretched to 100% and 225% were measured for water. The films were helium plasma treated for 4 minutes each and the contact angles remeasured. The results are shown in FIG. 23.

In conclusion, the stress/strain data showed that the polyurethane biomer is suitable for expansion up to 225% for use as a stent coating. The contact angle indicated that the straining the film and plasma treatment are not deleterious to biocompatibility.

Surface Chemistry

X-ray photoelectron spectroscopy (XPS) is a useful technique to analyze plasma-modified surfaces. The changes in surface chemistry from the outermost 100 A can be estimated using XPS. The XPS spectrum provides a spectral plot of photoelectron intensity against binding/bonding energy, where the spectral peaks are characteristic to specific atomic and molecular orbital. The spectral plot provides information on the elemental composition (except He and H) and nature of bonding within the molecule. The changes in bonding due to atmospheric plasma treatment can be reliably detected using an XPS. The objective is to correlate the changes in surface chemistry to the endothelial cell growth and adhesion on the polymer surface.

Figure 24A:
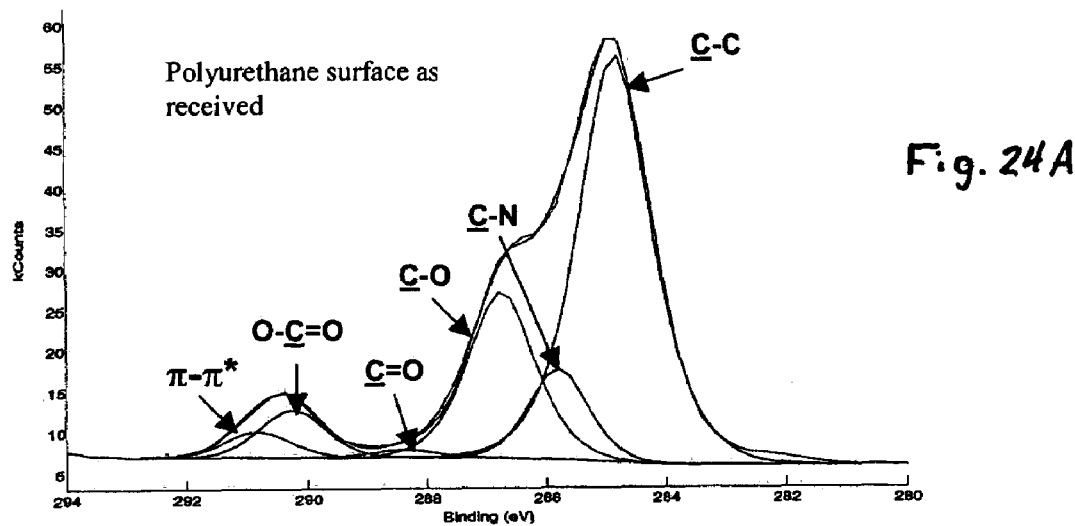
FIGS. 24A-C are graphs showing XPS results from untreated and plasma treated polyurethane.
Figure 24B:
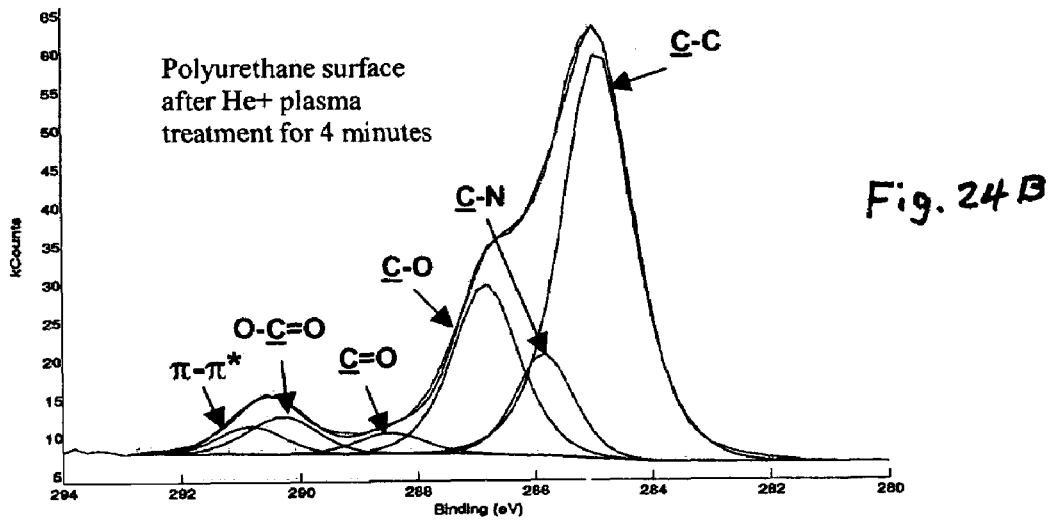
Figure 24C:
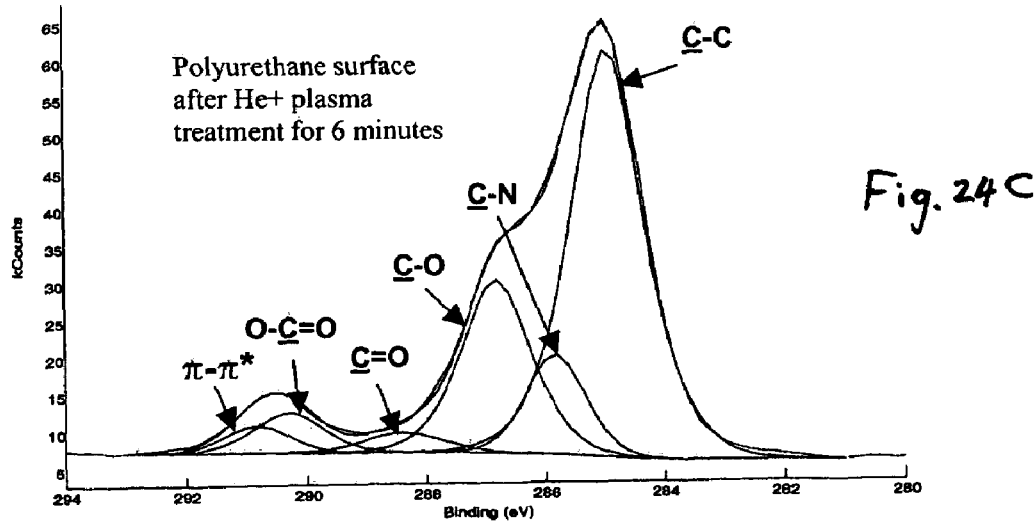

XPS data of the carbon peak of polyurethane before and after plasma treatment are shown in FIG. 24, and the peak summary is presented in Table 5 following:

|  | C—C | C—N | C—O | C=O | 0-C = 0 | $\pi$-$\pi$* |
|---|---|---|---|---|---|---|
| As rcvd. | 58.7 | 10.0 | 21.7 | 0.88 | 5.7 | 3.0 |
| He+4 mins | 57.0 | 10.8 | 21.7 | 2.6 | 4.8 | 3.2 |
| He+6 mins | 56.5 | 10.7 | 22.0 | 2.7 | 4.9 | 3.1 |

From the data it was observed that there were only minor changes after plasma treatment. There was a decrease in the C—C/C—H bonding and an increase in the C=O bonding indicating an increase in the oxidation of the surface. The synthesis of the ChronoFlex AR is carried out by the addition of MDI to polycarbonate diol, with the addition of a mixture of chain extenders and a molecular weight regulator, of which the composition of the latter two are unknown. Therefore at the present, it is difficult to get an accurate interpretation of the relevance of the XPS data. However, identification of the surface functional groups in correlation with surface tension data can enable the amount of hydrophilicity to be determined.

Figure 25A:
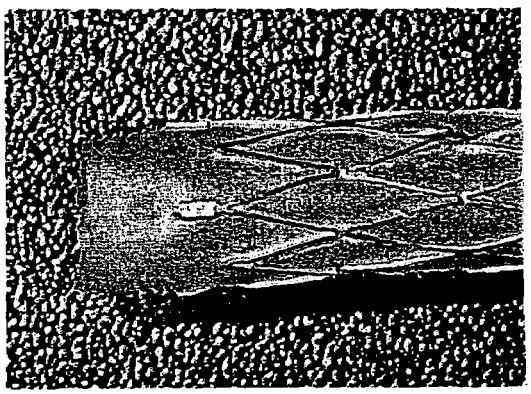
FIGS. 25A and 25B are micrographs of coated 3 mm stent.
Figure 25B:
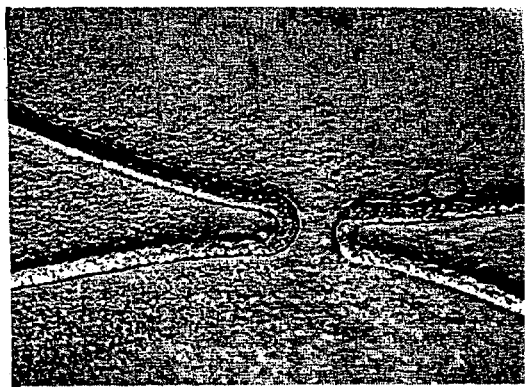

Once a stent is implanted and expanded, the strained coating has to hold its integrity. As shown earlier in FIG. 18 at the final equilibrium point c, the coating will be under tension by the struts of the stent framework. The forces have to be in balance so that there is no delamination of the coating from the metal. At present, stents are electropolished as their final finish, which produces a very smooth, corrosion resistant surface. But if the stents are to be totally encapsulated, then this smooth surface may no longer be needed. Optical images of a 3 mm polyurethane coated stent are shown in FIGS. 25A and 25B. Good coverage was achieved with no gaps between the struts observed.

The next step was to test the performance of a simulated coated stent. As the tubular shape of a stent prevented it from being utilized in the Instron, a model was made. A stainless steel wire of 500 μm diameter was threaded on a jig to form a simulated stent pattern. The pattern was placed on a pre-prepared thin polyurethane film (~50 m), and re-coated. A coated stent model was then produced. The film pattern and cross-section is shown in FIGS. 26A and 26B.

High magnification optical images were taken of the wire coating integrity before elongation. These are shown in FIGS. 27A-F, where it can be seen that the coating was uniform even around the curves of the wire. The total film thickness of the coating between the wires was measured at approximately 125 μm.

A coated stent model model was placed in the grips in an environmental chamber on the Instron. An optical microscope with video camera was set-up outside the environmental chamber so that the induced strain was recorded during the tensile test. Images of part of the wire taken at various points in the test up to 50% strain and on unloading are shown in FIGS. 28A-L. The corresponding stress/strain curve is shown in FIG. 29.

Stretching of the polyurethane film from the wire was first observed at 13.3% strain. It appears to be pronounced around a bend in the wire. At 50% strain, slight separation from the wire is also observed on a straight part of the wire that was not seen in earlier images. Upon unloading, a marked delamination region was observed at 20% strain, however, this is not so pronounced upon complete unloading (0%), and the coating appears similar to before the test. The stress/strain curve shows a residual strain after unloading for the coated wire of 20%, which was slightly lower than the 26-28% observed for plain films.

Figure 30:
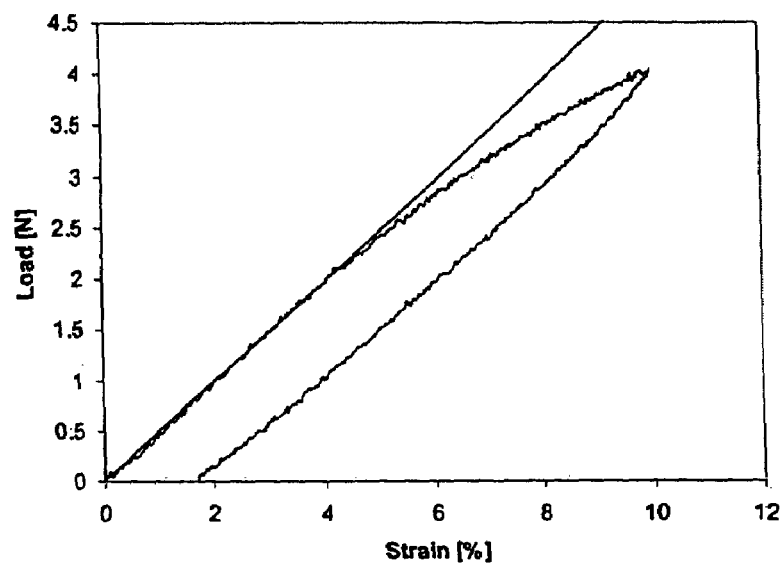
FIG. 30 is a stress/strain curve for polyurethane coated stainless steel wire (10% strain).
Figure 31A:
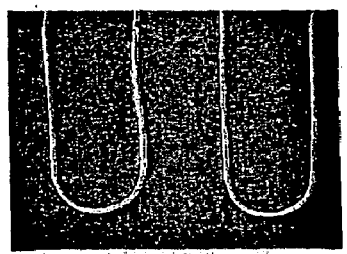
FIGS. 31A-F are optical images of coating on wire after straining to 10%. No delamination is observed.
Figure 31B:
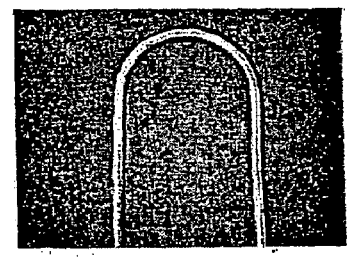
Figure 31C:
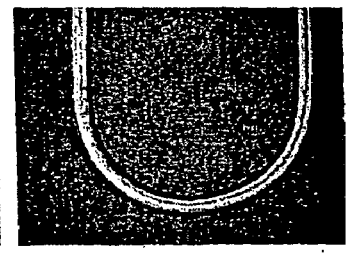
Figure 31D:
Figure 31E:
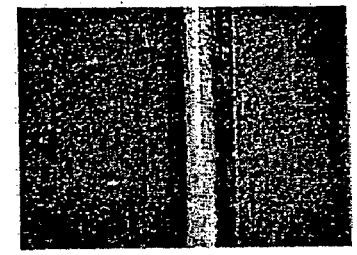
Figure 31F:
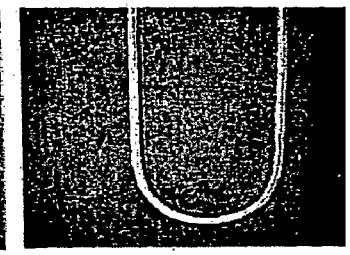

A second film including a wire was made. This film with wire was tensile tested to 10% strain, as shown in FIG. 30. For this experiment, less than 2% residual strain was observed. Once again, the load required to produce 10% strain was higher than for the film alone. Observation of the coating after testing showed no signs of delamination of the coating from the wire as shown in FIGS. 31A-F.

The objective of the work performed to date was to investigate the mechanical properties of ChronoFlex AR polyurethane as a viable coating for cardiovascular stents. It is estimated that expansion of a stent once placed in an artery will cause as much as 225% expansion circumferentially. Any coating will therefore have to be able to withstand a 225% strain without breaking down in the bodies' environment. The data show that the polyurethane when cast as a thin film and cured in air, showed significant residual strain when strained to 50,% with possible residual microtears and compromise of the structural integrity. Strain of a coated steel wire to 10% strain showed minor residual strain (<2%), but no delamination of the film from the wire was detected.

Drug Incorporation in Polyurethane Coatings

To prevent restenosis and thrombogenicity, drugs could be incorporated into the polymer coating. The drugs can deliver a localized dosage as cell growth inhibitors. Possible methods of drug coating are: 1) a solution of a liquid polymer and drugs, 2) deposition of dry dispersed drug particles into the coating, and 3) nebulized drug particles in the coating. Creating a coating-drug homogenous matrix will allow for a specific concentration of the drug within the coating, but if the polymer is slow to corrode within the body, the drugs may not be released at an effective rate for long-term beneficial effects. Particle deposition improves the drug's time-release effect. Particles of the drug are deposited upon the polymer coating while it is still wet. Larger particles will sink to the lower levels of the polymer coating and smaller particles will remain suspended within the polymer coating or along the surface of the coating. Therefore, as the coating is corroded, there is a constant delivery of drugs within the artery. The concentration of the administered drugs at any given point in time is not easy to control with this method, however, as is the distribution of the coating. The third technique, nebulization, allows for an extremely even distribution of drugs, comparable to the coating-drug matrix. Drug particles are nebulized in an aqueous solution. The atomized droplets from the solution are impacted against a plate to remove large droplets, creating a very even distribution of droplets. The solvent then evaporates, leaving an evenly dispersed layer of drug particles. The maximum size of the particles can be controlled to form a uniform layer of polymer coating containing drug particles. The particles that remain close to the surface of the coating will have a fairly extended time-release effect for the dissolution of drugs.

The basic application of drug incorporation in stents is to prevent the thrombus formations within the arterial wall along the stent. A thrombus consists of agglomerated platelets that deposit along the arterial wall, restricting blood flow. In some cases, the thrombus may become detached and released into the bloodstream (embolization), where it may cause a stroke or heart attack. The model for a thrombus formation is as follows:
1. Proteins (fibrinogen) adhere onto the stent surface
2. Platelets aggregate and fibrinogen clots into fibrin.
3. Activation of macrophages
4. Giant cell formation
5. Thrombus formation and
6. Restenosis or Embolization (detachment)

The desired effects of drug delivery are the prevention of the activation of fibrinogen by thrombin and the attachment of fibrin, followed by platelet aggregation, and thrombus formation. The entire inner wall of the stented region of the artery should have a coating with an anticoagulant drug or endothelial cells that inhibit protein adhesion or platelet deposition.

Producing Aspirin Aerosol for Coating with a Nebulizer

A nebulizer is a device to atomize a liquid into tine droplets. A high velocity air jet emerging from a fine nozzle creates a low pressure at the exit section of the jet. The liquid to be atomized is placed inside a glass or plastic bottle. A liquid feed tube is used, one end of which is submerged within the liquid and the other end is placed perpendicular to the air jet nozzle located inside the bottle. The high velocity air jet causes the liquid to rise up in the feed tube and be atomized into a mist of fine droplets of a diameter ranging from 5 to 15 μm. The liquid being nebulized may contain a solute or a suspension of fine solid particles. The droplets are allowed to dry in air to form solid particles. The solid particles are much smaller in diameter compared to the droplets depending upon the concentration of solute within the droplets. The nebulization method, therefore, allows the solute to form fine particles, in the range of 0.5 to 2.0 μm in diameter. The aspirin solution was nebulized to produce aspirin aerosol.

Two tablets of aspirin, each containing 325 mg of aspirin, was dissolved into 250 ml of distilled water for nebulization. The aspirin concentration was 25 mg/ml. The cloud of aspirin particles was allowed to flow through a chamber where microscope slides and stent coupons were placed. The particles were deposited on the surface of the polyurethane coating.

Mathematical Model for Drug Incorporation

The mass of embedded drugs on the wire mesh was calculated by assuming each drug particle is spherical and that the particles were deposited as a monolayer forming concentric rings. For a particle diameter of 10 μm, each particle will require an area of $7.5\times10^{-7}$ $cm^2$ on the substrate. Assuming 60% of the surface area of the substrate is covered by the drug particles, there will be $1.2\times10^5$ particles per $cm^2$. Assuming each particle has a density of 1 $g/cm^3$, then there will be 1.2 μg of the drug per $cm^2$ of the substrate. In an actual case, the wires used in the stents would be covered with a polymer coating incorporating one or more drugs.

Water and ions diffuse into a polymer coating when the coated metal is submerged in an electrolyte. Therefore, when the stent is implanted within the artery, the diffusion of water will provide a slow dissolution of the drug by the body fluid into the surrounding tissue. For drug-incorporation calculations, r is the radius of the drug particle, b is the separation between the layers of drug particles and the separation between each drug particle, and m is the number of layers of drug particles. SUM refers to the number of particles in one ring, R stands for the radius of the stent wire, L is the total length of all wires in the stent, P is the number of rings of drug particles along the length L of the stent wires, PAR- TICLES stands for the total number of particles on the stent, DRUGMASS stands for the total mass of drugs within the coating, and MP is the mass of each drug particle.

Number of Particles on $m^{th}$ layer:

$$n_m=(2\pi(R+mb+(2m-1)r))/(2r+b)$$

SUM:

$$\Sigma n_i = n_1+n_2+n_3+ \ldots +n_m$$

MP:

$$mass=4\pi r^3 d/3$$

For a maximum coating thickness of 50 µm, the maximum value of m was determined by the following equations in a C++ program:

$$mb+(2m-1)r=50 \text{ µm}$$

$$P=L/(2r+b)$$

DRUGMASS=SUM*P*MP

For a stent of 4 mm diameter, 40 mm long wire mesh tube, with a 50 µm thick polyurethane coating, the mathematical model shows that a maximum amount of 2 mg of a drug can be embedded if only the stent wires are coated. When the entire stent is encased, the amount of an incorporated drug in the coating will increase.

COS-7 Studies

The cells used for this research are COS 7 monkey kidney cells. Their properties resemble those of endothelial cells and the cell line is not as sensitive to its environment when compared with endothelial cells. A hemacytometer was used for counting the number of cells growing on each of the test surfaces. The hemacytometer grid is divided up in to sixteen squares, each $1/16 mm^2$ in area. Each square is further divided into sixteen smaller squares. An average number was taken in regards to the number of counted cells and used for calculating the total number of cells upon each substrate.

In order to study endothelial cell attachment, COS 7 cells were used as a pilot study since these cells are relatively easy to grow and do not require specially modified media. The next phase of biocompatibility studies are being conducted with endothelial cells. Current results therefore may not be an accurate portrayal of endothelial cell reaction due to the difference in the types of cells.

SEM Studies

The integrity of the coating was studied using a Scanning Electron Microscope (SEM). The results show that the film surface remained uniform after stress, simulating expansion of the coating around the stent within the artery.

Plasma Treatment of Polyurethane Coated Stents

Plasma modification is a surface modification technique used extensively in biomedical industry. In plasma modification technique, gases such as nitrogen, argon, oxygen are ionized under low pressure (0.1-1 Ton) and ambient temperature (25-60° C.). The ionization of gas generates an extremely reactive environment comprising of positive ions, negative ions, free radicals, atoms, molecules, and photons. Surfaces exposed to gas plasma can be cleaned, sterilized, and functionalized simultaneously. Atmospheric plasma is relatively cheap and reliable technique to promote biocompatibility. In atmospheric plasma, a plasma glow discharge is initiated under atmospheric pressure and ambient temperature. Inert gases such as helium, argon are effectively used to generate atmospheric plasma. Ratner and co-workers have shown that surface property such as elemental composition, nature of chemical bonds, and free energy can significantly affect the biocompatibility of the polymer (Ratner, B., et al., Biomaterials Science: An Introduction to Materials in Medicine, Academic Press, NY, 1996; Park, K., et al., Synthesis and Characterization of SPUU-PEO-Heparin Graft Copolymers, Journal of Polymer Science: Part A; Polymer Chemistry, Vol. 29, 1725-1737, 1991). Better understanding of the surface properties has led to different surface modification techniques to improve biocompatibility. Such surface modification techniques involves modifying a few molecular layers of the surface (25-50 Å) and attach various functional groups to promote factors such as blood compatibility, cell adhesion and growth, protein absorption, etc.

Surface modification of a polyurethane-coated stent is performed using a two step process. The first step is pretreatment of bare metallic stents (both Nitinol and SS) prior to polymer coating. Plasma treatment is performed in a low-pressure reactor using a reactive gas such as oxygen. This treatment has multiple effects. The free radicals generated in plasma remove any kind of contamination from the metal surface. The oxygen ions/molecules in plasma react with the metal surface resulting in generation of a thick passive oxide layer, which enhances corrosion resistance against biological fluids. Plasma treatment also increases the surface roughness, which improves adhesion of the polymer coating to the metal. A pair of copper electrodes (7.5 cm×3 cm) were placed across the reactor to generate a plasma as shown in FIG. 16A. This capacitively coupled plasma generator operated at a frequency of 700 Hz. The voltage across the electrodes was 12 $kV_{rms}$ (Root Mean Square Voltage). The pressure inside the plasma reactor was 0.03 torr.

The second step is the plasma treatment of the inner lining of the polyurethane film inside the encased stent to promote the growth of endothelial cells. The majority of the commercially available plasma treatment reactors are designed for flat substrates, where entire surface is exposed to plasma. These reactors cannot be used effectively to modify the inner lining of a stent. The metallic mesh of the stent acts as Faraday cage and does not allow the electric field to penetrate from the outer wall to the inside. The Faraday cage effect prevents the generation of plasma inside the stent and hence the effective surface modification. This reactor has been designed for plasma surface modification of inner lining of polyurethane coated stent at atmospheric pressure. Surface modification is required to promote the growth of endothelial cells on the inner lining of stent. The reactor consists of a coaxial central electrode through the stent connected to a high voltage power supply and a metal metal mesh outside acting as ground electrode as shown in FIG. 16B. Sine the electric field is confined within the stent the plasma is also confined inside the stent. Thus it does not modify the outer surface of the stent. Another unique aspect of this design is that this reactor operates under atmospheric pressure as compared to low pressure reactors for nearly all biomedical applications. The plasma treatment not only promotes endothelialization but also effects sterilization, which is extremely important for any biomedical implant.

The atmospheric plasma reactor is made of a cylindrical Pyrex glass tube (30 mm inner diameter, 90 cm long) with inlet connected to a gas flow regulator and outlet connected to an exhaust. A pair of copper electrodes (7.5 cm×3 cm) is placed across the reactor to ionize the gas. This capacitively coupled plasma generator is operated at a frequency of 700 Hz. The voltage across the electrodes was 12 $kV$,-ms (root mean square voltage). Polyurethane-coated glass cover slips and Nitinol coupons were placed inside the reactor between the copper electrodes, and trace quantities of helium gas is introduced into the glass tube. The plasma treatment was usually carried out for 6 minutes. However, for XPS studies plasma treatment was also performed for different length of times.

An atmospheric pressure helium plasma treatment of polyurethane coating showed a significant growth of endothelial cells as compared to untreated polyurethane coating.

Atomic Force Microscopy (AFM)

Atomic force microscopy (AFM) is used to characterize the topography of polymer surfaces. Surface roughness measurements can be performed on images acquired from surface scans using an etched silicon probe (TESP-type) on a non-contact tapping mode. The typical roughness parameters are defined as follows:

1. Mean Roughness ($R_a$): The arithmetic average of the deviations from the center plane.
2. Root Mean Square ($R_q$) Roughness: The standard deviation of Z values over a given area.
3. $R_{max}$: The difference of height between the highest and lowest points on the surface relative to the mean plane.
4. $\Delta A_{True}/\Delta A_{App}$: The percentage increase of the three-dimensional surface area over the two-dimensional surface area.

The objective is to measure any significant change in the measured roughness parameters due to plasma treatment of the polymer surface and correlate such changes to endothelial cell growth adhesion.

A Dimension 3100™ Scanning Probe Microscope (SPM) manufactured by Digital Instruments, CA was used for acquiring high-resolution optical images and performing surface scans. Surface scans were performed on non-contact tapping mode using an etched single crystal probe (RTESP). The scanning frequency varied from 1 Hz to 2 Hz for large area (100 µm×100 µm) and small area (1 pm×1 pm) respectively. The phase and height images were acquired simultaneously for smaller area (1 pm×1 pm) scans. The large area scans (100 µm×100 µm) were utilized for estimating roughness parameters. Roughness measurements of the whole image or a specific area of the image can be performed by using computer programs based on Fast Fourier Transform (FFT). The roughness parameters estimated by the software, provided by Digital Instmments, were $R_a$, $R_q$, $R_{max}$ and $\Delta A_{True}/\Delta A_{App}$.

Protein Depositions Studies

Biomaterials in general interact with proteins when used as implants. Soluble proteins present in biological fluids such as blood plasma are known to interact with biomaterial surfaces before cell attachment. Therefore, before studying endothelial cell growth, human albumin and fibrinogen was used to examine if these proteins are adsorbed on stainless steel or Nitinol coupons. Fluorescein isothiocyanate conjugated albumin (FITC-albumin) and fibrinogen was obtained from Sigma Chemicals. Working solutions of 1 mg/ml were prepared in PBS. Metal coupons were incubated with the protein samples for 1 hr. at 37° C. and then washed with excess PBS to remove unbound proteins. Bound albumin was directly visualized under fluorescence microscope. Fibrinogen binding was detected immunologically using an antibody to human fibrinogen and a secondary antibody conjugated with FITC. Appropriate controls were included to check any background fluorescence.

Endothelial Cell Growth Studies

The polyurethane-coated stent with a homogenous layer of endothelial cells on the inner wall of the stent prevents restenosis by inhibiting the conversion of fibrinogen to fibrin and platelet aggregation. Our studies indicate that atmospheric helium plasma treatment of polyurethane surface enhances endothelial cell growth. Cell growth on plasma-treated polyurethane coatings was greater than on the untreated polyurethane coatings (57,000±1,250 vs. 6,650±1,250 per cm$^2$). The collagen-coated polyurethane coatings were found to be most suitable for endothelial cell growth (82,500±7,500). A flow cell as shown in FIG. 17 is used for both studying cell growth in a simulated blood flow and to compare the stent wall induced turbulence with and without stent wire encasement. Human coronary artery endothelial cells (HCAECs) are used for seeding the inner wall of the encased stent and cultured. A variable-flow, self-priming, peristaltic pump is used to initiate laminar flow ($N_{Re}$<2100) of Newtonian fluids, such as saline or Ringer's solution, through the flow cell. To examine the effect of turbulence, a fine jet of dye is introduced at the upstream of the flow stream and the mixing of the dye with the serum is examined at the downstream of stent. The coating process is optimized to minimize turbulence created by the stent wires and the associated edge effect by appropriate film formation and smooth transition. The flow cell is also used to study cell adhesion on polyurethane surface under different shear stress.

A Clonetics human coronary artery endothelial (HCAE) cell system was obtained from Cambrex Bio Science Walyersvilie, Inc. This system contains normal coronary artery endothelial cells and optimized media for growth. Endothelial cells were recovered from cyropreserved vials by quickly thawing at 37° C. and resuspending them at 12 mL complete medium (Clonetics EGM-2 supplemented with 5% fetal bovine serum and a combination of growth factors). Resuspended cells were plated in a 75 cm$^2$ flask and grown in an incubator at 37° C. and 5% $CO_2$. After four hours of initial seeding from cyropreservation, the medium was replaced with a fresh medium. The medium was then changed every 2-3 days. At confluence, the endothelial cells were detached by trypsinization (0.025 Trysin/0,0 1% EDTA) and sub-cultivated at a density of 2,500-5,000 cells/cm$^2$ for further propagation. The cells were frozen in liquid nitrogen for storage, if needed, in a freeze medium consisting of culture medium (95%) and DMSO (5%). Control experiments of cell culture were performed on Fisherbrand® glass cover slips and sterilized Nitinol coupons. Confluent cell growth is generally achieved after 3-5 days of cell seeding. The above protocol was followed for cell cultures on uncoated and polyurethane-coated surfaces following surface modifications. Polyurethane surface modifications were carried out either by protein deposition or helium plasma treatment. For collagen and fibronectin coating, 0.1% stock solutions prepared in 0.1 N acetic acid solution were diluted to 0.01% working solution in Phosphate Buffer Solution (PBS). The spun coated glass cover slips and Nitinol coupons were incubated with 2 ml of working solutions of the proteins at 37° C. for overnight. For gelatin coating over the polyurethane coatings, a pre-formulated 0.01% gelatin solution obtained from Sigma-Aldrich was used. Prior to cell culture, the excess solution was removed and the coatings were dried under UV light.

In order to visualize endothelial cells grown on polyurethane non-transparent surfaces, a fluorescence dye, acridine orange (Molecular Probe, Inc.) was used. A stock solution (0.1 mg/mi) was prepared by adding acridine orange on Phosphate Buffer Solution (Cambrex Bio Science Walyersville, Inc.). The stock solution was further diluted (1:50 v/v) in PBS for staining purposes. The polyurethane coatings were taken out of the incubator after appropriate cell confluence and then treated with acridine orange solution (1:50 v/v) for 1-2 mm. The cover slips or the coupons were then washed with excess PBS and immediately placed under fluorescent microscope for visualization. The stained endothelial cell under fluorescent light appeared yellowish to orange with normal elongated shape dispersed randomly on a black background. Photomicrographs of stained HCAE cells were obtained using Nikon camera integrated to the microscope. Five representative fields were selected from each type of surface treatment for cell counting purposes. The number of stained cells counted from the each field was converted to cell density (number/cm$^2$) after area correction. The mean and standard deviation of the cell density counted from five to nine fields was reported. Traditional cell counting was also done to compare the cell counting protocol using fluorescent staining procedure. The endothelial cells were detached from the polyurethane coatings or the cover slips by trypsinization (0.025 Trypsin/0.01% EDTA) and cells were counted using a hemacytometer under an optical microscope.

The critical surface tension of polymer surface is significantly affected by the surface chemistry. Typical polymer surfaces with atomic constitution of C, N, 0, and H has critical surface tension ranging from 30 to 40 dynes/cm. The ratio of the atomic constituents (C/H, C/N, C/O) also play a significant role in affecting the critical surface tension of the polymer surface. The chemical bonds such as π-π*, O—C=O, C=O, C—O, C—N were identified from the XPS analysis of the untreated polyurethane surfaces. These bonds were consistent with the polyurethane chemistry. Plasma treatment resulted in oxidation which is evident from increase of carbony (C=O) bond. The significant increase in carbonyl bond is expected to improve the wettebility of the polyurethane surface.

The tensile properties of polyurethane are based on formation of distinct phases of hard (aromatic isocyanate and chain extender groups) and soft segment (polyol). FIGS. 32A and 32B illustrate the microphase separation of hard and soft segments under 0% strain and after curing under 80° C. The spherical and elongated hard segment (90° phase) is dispersed on soft segment (0° phase). The higher occurrence of hard segment illustrates good tensile properties of the polyurethane coating.

Figure 34A:
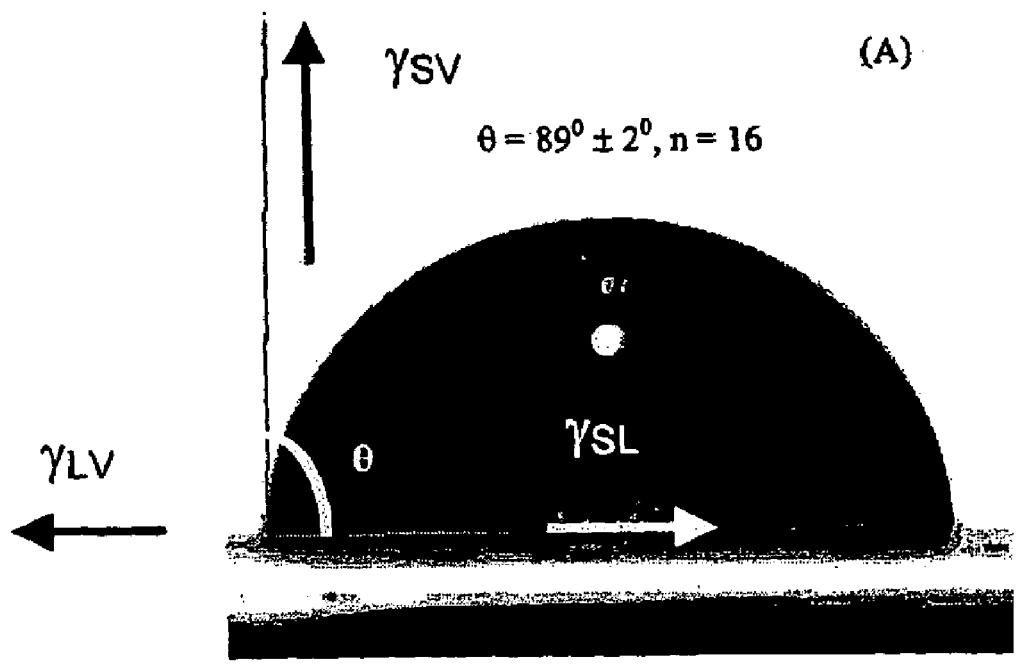
FIGS. 34A and 34B are diagrams illustrating contact angle measurements of distilled water on untreated and plasma treated polyurethane surfaces, respectively. The analysis was performed at 23° C. and 53% RH.
Figure 34B:
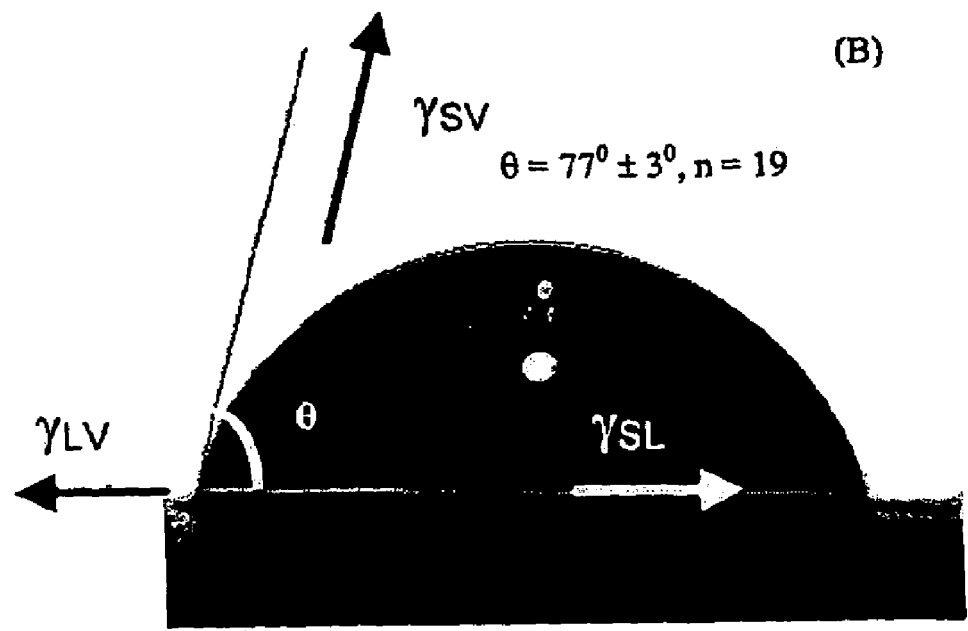

FIGS. 33A and 33B shows the surface topography of the spun coated polyurethane coatings and the roughness measurements were estimated from the image analysis. No significant changes in the surface roughness parameters between untreated and plasma treatment was observed. It was also observed that the roughness parameters of hard segments (90° phase) were in the micrometer range, while the roughness parameters of the soft segments (0° phase) were in the nanometer range. FIGS. 34A and 34B show a representative contact angle measurement of distilled water droplet on the polyurethane surface exposed to ambient air. A significant change ($p<0.05$) in contact angle was observed between the untreated and plasma treated surfaces. This also indicates that the plasma treated surfaces are more hydrophilic than untreated surfaces. Protein deposition studies show that stainless steel allows protein deposition. Fluorescence microscopic studies showed that human fibrinogen (FIG. 35A), as detected immunologically by anti-fibrinogen antibody and fluorescence labeled secondary antibody, and fluorecein isothiocyanate conjugated albumin (FIG. 35B) were bound to stainless steel coupons. Similar studies were also found using Nitinol coupons.

Figure 36A:
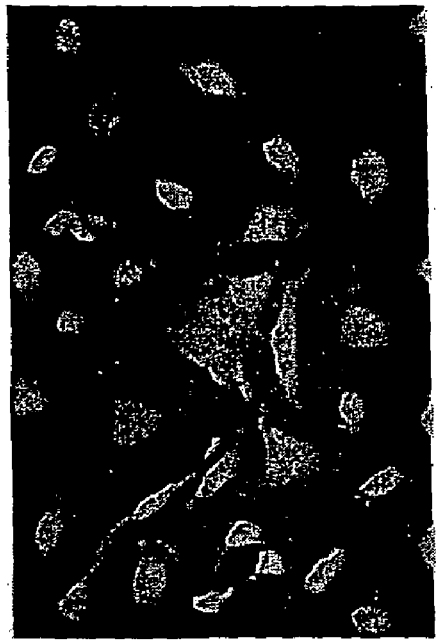
FIGS. 36A-D are fluorescence photomicrographs of aricidine orange stained HCAE cells on glass cover slip, stainless steel coupon, polyurethane coated glass cover slip, and polyurethane coated stainless steel coupon, respectively.
Figure 36B:
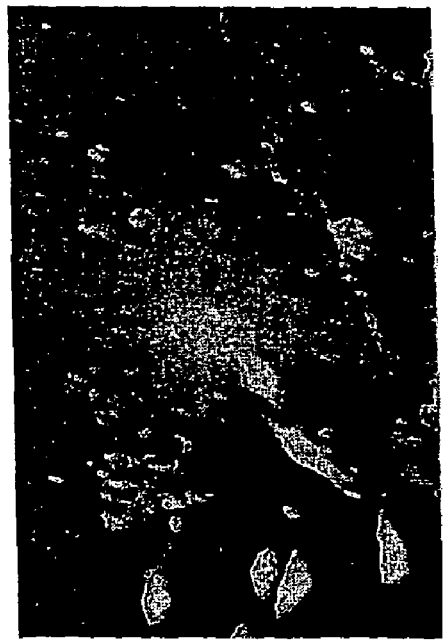
Figure 36C:
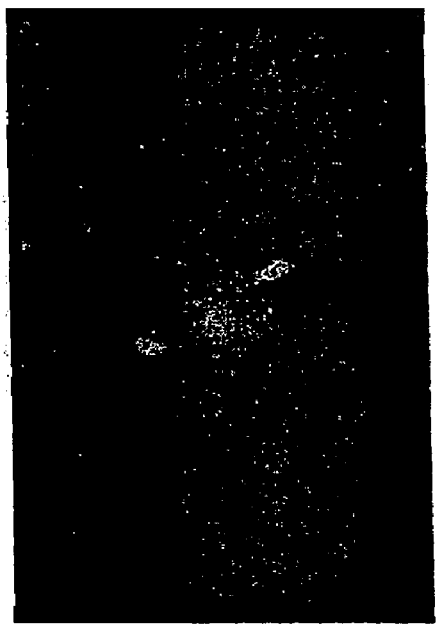
Figure 36D:
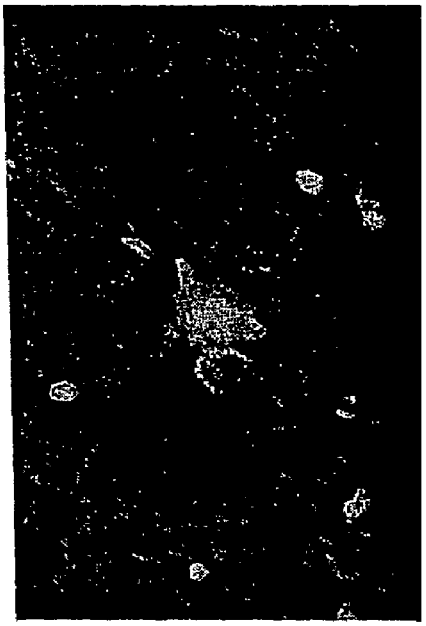
Figure 39A:
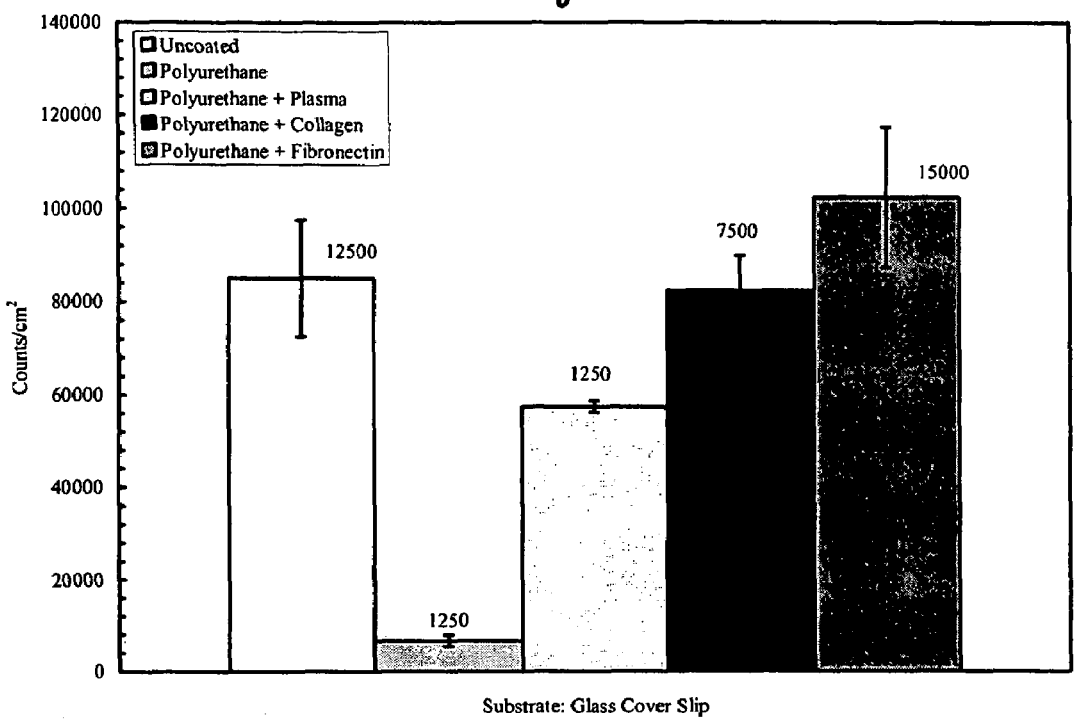
FIGS. 39A and 39B are graphs of endothelial cell counts on polyurethane-coated glass cover slips and stainless steel coupons, respectively. Cells were counted from different fields after fluorescence staining. Number of cells optimized per $cm^2$ and represents average+/−standard errors from 5-9 fields under the same magnification.
Figure 39B:
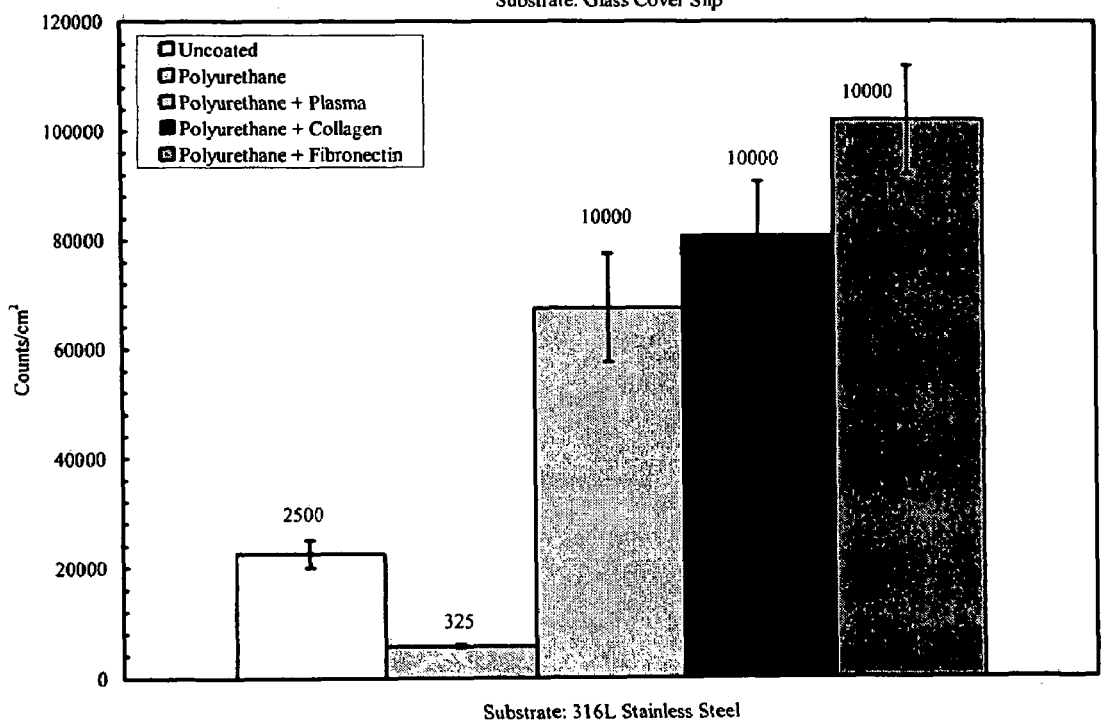

The Human coronary artery endothelial (HCAE) cells were normally grown in glass petri dishes or on glass cover slips. Following fluorescence staining, normal endothelial cells grown on glass cover slips appeared elongated (approximately 100 pm in long and 20-50 pm wide) uniformly distributed on the substrate FIG. 36A. However, stainless steel coupons did not support normal cell growth. The cell growth was reduced by more than 90%. The size of the cell on the bare metal coupon was also reduced considerably (FIG. 36B). When cells were grown on polyurethane coated surfaces (glass or metal) without any treatment to the polymer surface, cells did not grow as normal. This may be due to the fact that this polymer does not provide surface properties that are required for normal cell growth. It may also be possible that the polymer itself is toxic to the cells. We studied polymer surface modifications following coatings on glass cover slips (FIGS. 37A-C) as well as metal coupons (FIG. 38A-C) in an attempt to maximize endothelialization. When the polymer surfaces were treated with helium plasma, the cell growth was enhanced dramatically close to a normal level (FIGS. 37A & 38A). This polymer surface modification is known to enhance hydrophilicity of the polymer and introduces some functional groups, which might have affected cell growth. We also compared endothelial cell growth patterns on plasma modified polyurethane surfaces with those polyurethane surfaces obtained by protein coatings. Polyurethane surfaces were treated with collagen and fibronectin and then seeded with endothelial cells. As is evident from FIGS. 37B,C & FIGS. 38B,C, protein coated surfaces allow maximum cell attachment and growth which is comparable to the plasma treated surfaces. The cell counting was done by image analysis of fluorescence photomicrograph obtained using various treatments. The data shown in FIGS. 39A and 39B indicates that the plasma treatment of the polyurethane surface enhances the growth of endothelial cells, which is comparable to the cell growth observed with collagen and fibronectin treatments. Poor cell growth on untreated polyurethane coatings may be due to lack of adequate hydrophilicity or the presence of some toxicants as contaminants. Silicon contamination on the surface may also affect cell growth. When cells were counted using hemocytometer following trypsinization, large variations from cell density estimated from image analysis were observed. Such variations may be due to loss of cells during the trypisinization process. The average cell density from a representative experiment out of three performed separately show an estimated counts on glass cover slips, polyurethane coatings, and helium plasma treated polyurethane coatings as 14322, 1666 and 5280 respectively. Nevertheless, this again provided a clear indication that plasma treatment enhances endothelialization.

The present invention has been described with reference to certain preferred and alternative embodiments that are intended to be exemplary only and not limiting to the full scope of the present invention as set forth in the appended claims.

What is claimed is:

1. An encased stent comprising:
 a substantially tubular body comprising a plasma-treated wire mesh; and
 an encasing coating, comprising
 a first layer of a conducting biocorrosion-inhibiting material on said wire mesh;
 a second layer of polyurethane forming a substantially continuous film;

a third layer of polyethylene glycol; and a coupling agent for coupling said second layer of polyurethane to said third layer of polyethylene glycol.

2. The encased stent of claim 1, wherein said encasing coating comprises at least one therapeutic agent selected from the group consisting of an anti-thrombin drug, an anti-inflammatory drug, an anti-coagulant drug, a cell cycle inhibitor and a vascular endothelial growth factor.

3. The encased stent of claim 1 where said conducting biocorrosion-inhibiting material comprises ligno-pani.

4. The encased stent of claim 1 where said coupling agent is toluene diisocyanate.

5. The encased stent of claim 1, wherein said encasing coating comprises an inner surface and an outer surface, further comprising a layer of endothelial cells on said inner surface.

6. The encased stent of claim 5, wherein said inner surface is plasma-treated.

7. The encased stent of claim 1 further comprising means for producing a substantially smooth encasing coating when the stent is expanded radially.

8. The encased stent of claim 7 wherein said means for producing a substantially smooth encasing coating comprises a plurality of thickened regions of said encasing coating between said wires and a plurality of thin regions of said encasing coating in proximity to said wires.

* * * * *